United States Patent [19]

Langer et al.

[11] 4,407,288
[45] Oct. 4, 1983

[54] IMPLANTABLE HEART STIMULATOR AND STIMULATION METHOD

[75] Inventors: Alois A. Langer, Pittsburgh; Steve A. Kolenik, Leechburg; Marlin S. Heilman, Gibsonia, all of Pa.; Mieczyslaw Mirowski, 2405 Velvet Valley Way, Owings Mills, Md. 21117; Morton M. Mower, Lutherville, Md.

[73] Assignee: Mieczyslaw Mirowski, Owings Mills, Md.

[21] Appl. No.: 243,801

[22] Filed: Mar. 16, 1981

Related U.S. Application Data

[63] Continuation-in-part of Ser. No. 215,275, Dec. 11, 1980.

[51] Int. Cl.$^3$ .............................................. A61D 1/36
[52] U.S. Cl. ......................... 128/419 PG; 128/419 D
[58] Field of Search ..................... 128/419 D, 419 PG

[56] References Cited

U.S. PATENT DOCUMENTS

| | | | |
|---|---|---|---|
| 3,805,795 | 4/1974 | Denniston et al. | 128/419 D |
| 3,857,398 | 12/1974 | Rubin | 128/419 D |
| 3,952,750 | 4/1976 | Mirowski et al. | 128/419 D |
| 4,055,189 | 10/1977 | Auerbach et al. | 128/419 PG |
| 4,114,628 | 9/1978 | Rizk | 128/419 D |

FOREIGN PATENT DOCUMENTS 4243 9/1979 European Pat. Off. ..... 128/419 PG

Primary Examiner—William E. Kamm
Attorney, Agent, or Firm—Fleit, Jacobson, Cohn & Price

[57] ABSTRACT

An implantable heart stimulator and related method calls for the determination of a given heart condition from among a plurality of conditions, the selection of at least one mode of operation for treating the determined condition, and the execution of the mode of operation selected, so as to treat the determined condition. In one embodiment of the invention, wherein a plurality of modes of operation for treating the various conditions are provided, the implantable heart stimulator includes processors, each processor being designed to efficiently execute a respective group of modes of operation. A further embodiment of the present invention calls for the implantable heart stimulator to be implemented by at least one programmable microprocessor. A still further embodiment calls for the provision of a data input-/output channel, by means of which data can be provided to and retrieved from the implantable heart stimulator. Operations carried out by the implantable heart stimulator includes cardiac pacing, cardioversion, and automatic defibrillation. In a further embodiment of the implantable heart stimulator and related method, sensing circuitry is provided to determine the presence or absence of an R-wave of the heart, the absence of which causes a pacing operation to be implemented, further sensing circuitry being provided to determine the presence or absence of a forced R-wave of the heart, the absence of a forced R-wave causing ventricular defibrillation to be implemented.

37 Claims, 9 Drawing Figures

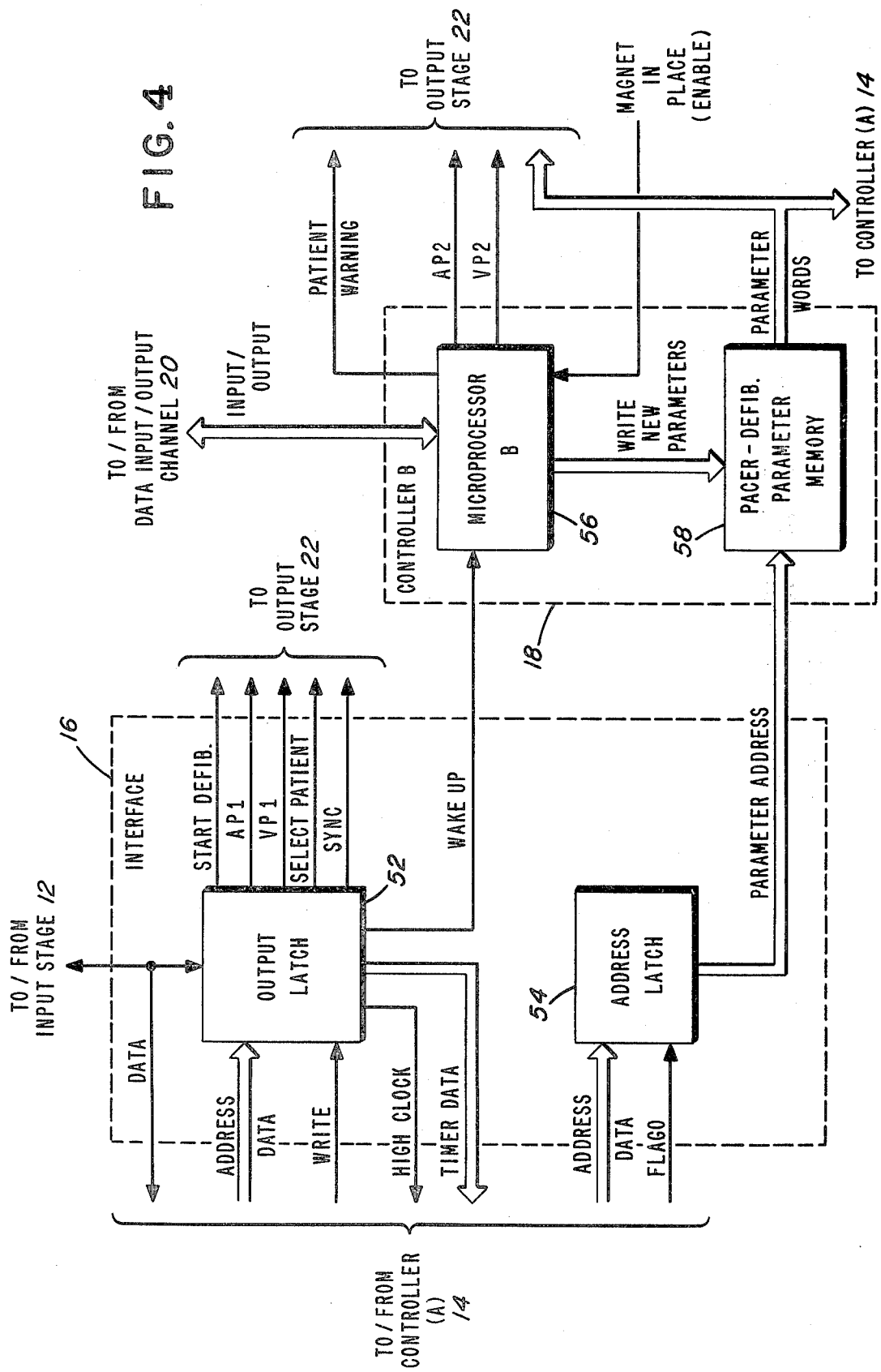

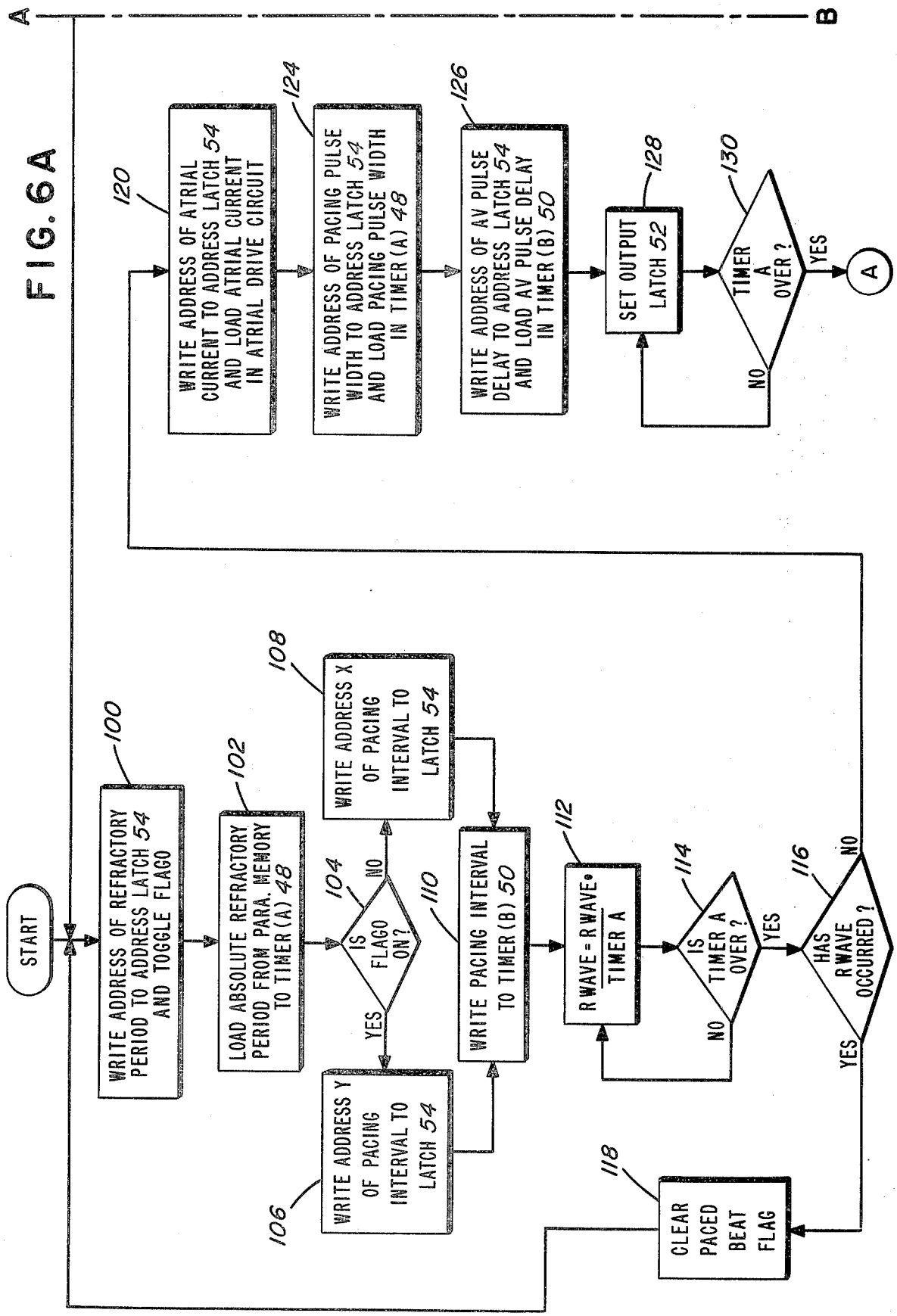

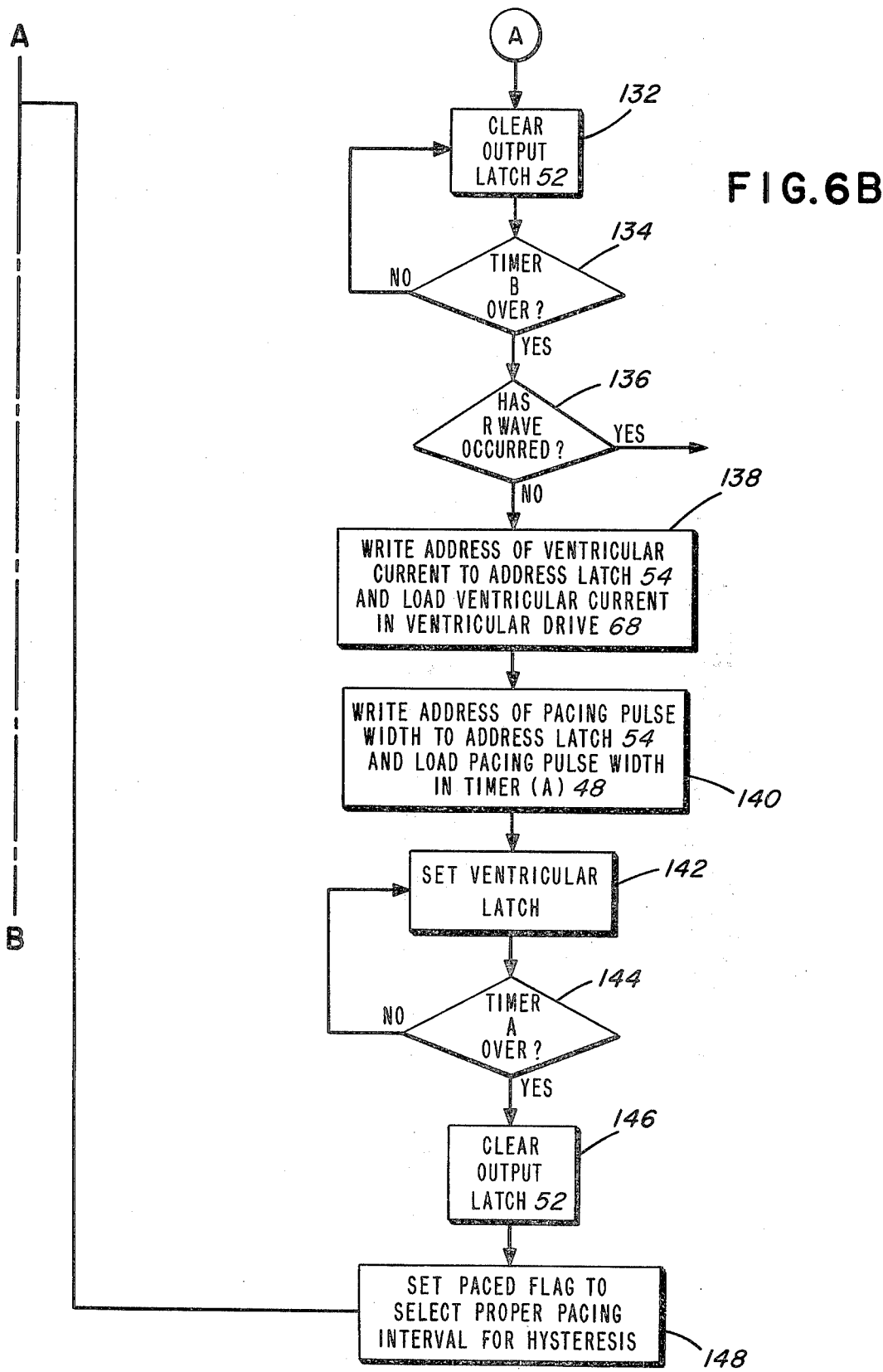

IMPLANTABLE HEART STIMULATOR AND STIMULATION METHOD

REFERENCE TO RELATED APPLICATION

This invention is a continuation-in-part of U.S. patent application Ser. No. 215,275 deposited Dec. 11, 1980, and entitled "Implantable Heart Stimulator and Stimulation Method".

FIELD OF THE INVENTION

The present invention relates to an implantable heart stimulator and related method, and more particularly to a highly versatile, externally programmable and implantable heart stimulator capable of functioning in various modes of operation to perform a variety of therapeutic routines in response to recognizable heart disorders or arrhythmias.

BACKGROUND OF THE INVENTION

In recent years, substantial progress has been made in the development of techniques for providing effective medical response to various heart disorders or arrhythmias. The types of contemplated disorders or arrhythmias have typically been treated in the past by drug therapy, or by devices such as pacers, defibrillators, cardioverters, etc.

More recent efforts have resulted in the development of electronic standby defibrillators, such as disclosed in U.S. Pat. No. Re. 27,652 of Mirowski et al (based on original U.S. Pat. No. 3,614,954) and U.S. Pat. No. Re. 27,757 of Mirowski et al (based on original U.S. Pat. No. 3,614,955).

Most recently, efforts have been directed toward the development of miniaturized defibrillating, cardioverting and pacing devices amenable to implantation in the body of a patient subject to heart disorder or arrhythmia. An example of one such implantable device is contained in U.S. Pat. No. 3,952,750 of Mirowski et al (which discloses a command atrial cardioverting device). The utilization of an implantable automatic defibrillator is referred to in U.S. Pat. No. 4,030,509 to Heilman et al. Moreover, U.S. Pat. No. 4,164,946 to Langer discloses a fault detection circuit for a permanently implanted cardioverter.

Despite the developments of the recent past, there remains much room for advancement in this area of medical technology. For example, it is considered highly desirable to develop a single implantable heart stimulator having the capability of selectively performing any one of the various techniques for responding medically to recognizable heart disorders or arrhythmias, that is to say, the development of a single implanted heart stimulator capable of performing defibrillating, cardioverting, and pacing functions on a selective basis.

It also is highly desirable to develop an implantable heart stimulator and related method capable of selectively performing any one of these techniques on an automatic basis, that is, automatically in response to detection of the occurrence of the corresponding heart disorder or arrhythmia.

Moreover, an extremely advantageous feature of such a device and method would reside in the capability of externally programming the device to perform various operations, or sequences of operations, in accordance with defined parameters. Further elaboration on this point, including a background discussion, is appropriate at this point.

It is known that the human heart requires coordinated electrical activity to successfully supply the body with a sufficient flow of blood. This coordinated activity is produced by a specialized conduction system contained in the body. A description of this system can be seen by reference to *The CIBA Collection of Medical Illustrations, Heart*, by Frank Netter, M.D., pp. 49-49, 1974 (ISBN 0-914168-07-X, Library of Congress Catalog No. 53-2151). Malfunctions of the conduction system produce a variety of human disease conditions up to and including death (see Netter, op. cit., pp. 66-68).

Recently, an implantable automatic defibrillator has been developed. The defibrillator automatically delivers a large electrical pulse to the fibrillating ventricles to abolish fatal malfunction and, thus, may be lifesaving in the case of ventricular fibrillation. Moreover, numerous other forms of electrical stimulation therapy have been, and are being, developed to treat various abnormalities of the heart.

For example, it is known that asystole (the absence of electrical stimulation to the ventricles of the heart) may be treated by implanting a pacer which periodically stimulates the ventricles with an electrical pacing pulse. Moreover, sophisticated pacing techniques, including various pacing modes (to be discussed in more detail below), have been developed.

Most automatic devices provide pulses to the atrium of the heart, but practitioners are reluctant to automatically treat the ventricle of the heart by pacing because of the dangers involved, for example, induced fibrillation. Accordingly, it is considered desirable to develop a device which has the capability of treating, by pacing modes and, if need be by backup defibrillation, any induced arrhythmia or fibrillation which might result from treatment of the ventricle of the heart.

It is presently known that electrical stimulation treatment modalities may be primarily classified in accordance with the energy level utilized, as follows:

| Pulse Type | Energy Range |
|---|---|
| Pacing | equal to or less than 100 microjoules |
| Cardioverting or defibrillating (internal) | 1-100 joules |

Stated in simple terms, pacing pulses stimulate a very small volume of heart tissue (approximately 1-10 mm$^3$), and the impulse is then contiguously conducted in a spreading fashion. Defibrillating pulses, on the other hand, are of sufficient strength to simultaneously stimulate all, or a critical mass, of the heart tissue, thus ameloriating the dangerous disorganized patterns of cyclic self-stimulation associated with ventricular fibrillation.

In the very recent past, combined pacing and cardioverting electrode systems have been developed, such as are described in U.S. Pat. No. 4,030,509 noted above. Such systems allow the delivery of defibrillating energy to either the atria or ventricles, and also allow for the delivery of pacing pulses. A large number of possible electrical stimulation options are thereby made possible from the combined electrodes.

Such combined pacing and defibrillating functions are quite effective in an implanted device because some symptoms, such as the absence of R-waves, could indicate an asystole (treatable by pacing) or life-threatening ventricular fibrillation. It therefore would be desirable to have a combined pacer-defibrillator that first could attempt pacing in the presence of such symptons, and then, if the symptons persist, attempt defibrillation.

A further copending patent application, Ser. No. 902,763 of Langer et al, is directed toward the development of a data recording device, intended for implantation along with an implantable automatic defibrillator. The intended purpose is to record approximately 100 seconds of the heart's electrogram before, during and after an episode of ventricular fibrillation. At a later time, the stored information may be extracted to provide a complete, permanent record of the ventricular fibrillation episode, including the operation of the device during automatic defibrillation. The use of this recording capability may be extended to capture critical data for additional modes of electrical stimulation therapy, and also to gain information which could lead to more effective future electrical stimulation.

Pacers are increasingly becoming programmable, whereby parameters such as pulse rate, pulse amplitude and R-wave sensitivity may be adjusted from an external device in electromagnetic communication with the implanted pacer. It would be highly desirable to implant a microprocessor within an implanted pacer/cardioverter, for a communication link could thus be established to enter data, such as a new program, changing the software program (and, hence, operation) of the microprocessor. Moreover, the presence of a microprocessor would allow the use of extensive logic and analysis in the diagnosis and treatment of heart malfunctions with various regimens of electrical heart stimulation. Thus, it is considered highly desirable to develop an implantable heart stimulator capable of performing more than one mode of electrical heart stimulation for a given malfunction, and further provided with the capability of utilizing a variety of parameters within any given mode of operation, and even further with the capability of employing logic in a variety of fashions.

Further referring to the employment of a microprocessor in an implantable heart stimulator, it is to be recognized that various microprocessors available today vary in both power consumption and speed, thus making certain microprocessors (of lower power and speed) suitable for long-term operations, while other microprocessors (of higher power and speed) are more suitable for performance of sophisticated operations on a short-term basis. Accordingly, it is considered highly desirable to provide an implanted heart stimulator with a dual processor capability. It is also desirable to provide the heart stimulator with both a high power, high speed processor and a low power, low speed processor. This would especially be advantageous in view of the further design criterion of providing an implantable heart stimulator having multiple modes of operation for performing various electrical heart stimulation techniques (as discussed above), since some operations would be suitable for performance by one processor, while others would be more suitable for performance by the other microprocessor.

Finally, there are times, during operation, when it would be preferable for a given processor to operate at a speed higher than its normal speed of operation. Thus, it is considered highly desirable for an implantable, microprocessor-based heart stimulator to have the built-in capability of "gear shifting" so that the microprocessor operates temporarily at a higher speed of operation.

SUMMARY OF INVENTION

According to the present invention, there is provided an implantable heart stimulator and related method, and more particularly a highly versatile, efficient, and externally programmable heart stimulator which forms an integrated system for carrying out electrical heart stimulation techniques (defibrillation, cardioversion, pacing, etc.) in response to the detection of various heart disorders or arrhythmias. Such an implantable heart stimulator is processor-controlled, and is preferably controlled by dual processors, each of the two processors being specifically chosen, by virtue of its design, for controlling a particular type of operation (long-term versus short-term, simple versus sophisticated).

To be more specific, the present invention relates to an implantable heart stimulator and related method capable of performing in a multiplicity of operating modes, each of which can non-invasively be activated. In addition, as will be explained below, various parameters for each mode are externally programmable. The long-term operating modes, to be performed by a simpler, slower, and less power-consuming processor, basically comprise: (1) ventricular fixed rate pacing, (2) atrial fixed rate pacing, (3) ventricular demand pacing, (4) bifocal pacing, and (5) automatic defibrillation. A short description of each mode is appropriate.

In the ventricular fixed rate pacing mode, the parameters can be programmed to various values. Such pacer parameters include pulse rate, rate limit, pulse amplitude (milliamperes), and pulse width (milliseconds). In a preferred embodiment of the present invention, an override capability exists, allowing the attending physician to double pulse rates (up to an appropriate maximum number of pulses per minute, e.g., 200 pulses per minute) for the purposes of overdrive. By activating the override mode, a burst of high rate pulses for a period of two to three seconds is issued. After this burst, the override is deactivated automatically and the pacer parameters return to original values.

In the atrial fixed rate pacing mode, the parameters can be programmed to various values, the parameters including pulse rate, rate limit, pulse amplitude and pulse width. In addition, an override capability exists, allowing the attending physician to cause a burst of rapid atrial pacing. In this mode, pulse rates can be increased by a factor of 10 over typical pulse rates, (50, 55, . . . , 115, 120 pulses per minute). Such a burst will last between 2 and 3 seconds, after which the pacer parameters return to their original values.

In the ventricular demand pacing mode, parameters can be programmed to various values; the parameters include pulse rate, rate limit, pulse amplitude, pulse width, sensitivity, and refractory period.

In the bifocal pacing mode, the parameters can again be programmed to various values, the parameters including pulse rate, rate limit, pulse amplitude, pulse width, sensitivity, refractory and AV (atrioventricular) delay.

Finally, automatic defibrillator operations can be performed in accordance with conventional parameters, including pulse energy (joules), number of pulses per sequence, and energy of each pulse. See, for example, U.S. Pat. Nos. 3,952,750 and 4,030,509.

Short-term operating modes, to be performed by a sophisticated, high-speed (and thus, high power-consuming) processor include: cardioversion, automatic patient warning, and automatic ventricular tachycardia control operations (including ventricular override pacing, rapid atrial pacing, ventricular coupled pacing, and automatic cardioversion). In addition, the more sophisticated and high-speed processor can perform, in a preferred embodiment, four-function recording, such recording being long-term in nature, but nevertheless performed by the high-speed processor, operating in the direct memory access (DMA) mode. A brief discussion of each of the latter operations is now appropriate.

In a preferred embodiment, the cardioversion mode is activated only by reception of an external command signal (such as detection of placement of a magnet on the surface of the skin adjacent to an implanted reed switch and the transmission of a word over the data channel). The output produced in the cardioversion mode is synchronized with the next R-wave following receipt of the command signal. Preferably, only one pulse per command is issued, and the pulse energies are non-invasively selected from among certain predetermined values (for example, 2, 5, 10, 15, 20, 25, 30 or 35 joules).

The automatic ventricular tachycardia control mode of operation is the most complex of all modes of operation implemented by the system of the present invention. This mode of operation can be implemented under program control, the implantable heart stimulator being pre-programmed and enabled by the physician. However, there exists also the capability of reprogramming the implantable heart stimulator, in correspondence to the results of the treatment thus far, and then enabling the operation of the heart stimulator so as to treat the patient further in accordance with the reprogrammed procedure. In this mode, any combination and/or sequence of the following sub-modes can non-invasively be selected (programmed) by the attending physician: ventricular overdrive pacing, ventricular coupled pacing, automatic cardioversion, and rapid atrial pacing. Any or all of these can be selected, so that, if the first response is not effective in controlling ventricular tachycardia, the next response is activated. That is, initially, a list associated with the various modes can be developed; then, the doctor can revise the list depending on the patient's reaction to treatment. A more detailed discussion of each of these sub-modes of operation now follows.

When ventricular tachycardia is detected, a two- to three-second burst of ventricular overdrive pacing is issued. The rate of overdrive pacing is pre-programmed at 10, 15, 20 or 25% above the sensed ventricular tachycardia rate. The number of bursts is pre-programmed at 1, 2, 3, or 4 before automatically proceeding to the next response mode. There is, typically, a five-second delay between bursts.

In the ventricular coupled pacing sub-mode, N ventricular pulses existing above a given rate cause a ventricular pacing pulse to be placed at a given time (expressed in percentage of the R-R interval) following the Nth ventricular pulse. In addition, if the tachycardia continues, a search mode comes into effect for which, after each Nth pulse, the coupling interval decreases by a given amount of time, until the final coupling interval is reached. This procedure can be repeated a number of times (preferably, up to four) before proceeding to the next response mode. Various parameters for this sub-mode of operation include the number of precursor pulses, the tachycardia rate (pulses per minute), the initial coupling interval (percentage of R-R interval), the coupling decrement (percentage), the final coupling interval (percentage), and the number of response cycles.

In the automatic cardioversion sub-mode of operation, when ventricular tachycardia is detected, an output pulse synchronized with an R-wave is issued. Up to four such pulses may be issued with any combination of pre-programmed energies (for example, 2, 5, 10 or 15 joules) before proceeding to the next response mode. There is, typically, a 5 second delay between each cardioversion pulse.

Finally, in the rapid atrial pacing sub-mode of operation, a two- to three-second burst of rapid atrial pacing is issued at a pre-programmed rate. The number of bursts before proceeding to the next response mode are pre-programmed at 1, 2, 3 or 4. There is typically, a five-second delay between each burst.

As stated previously, four-function recording constitutes a mode of operation which, although long-term in nature, is performed by the short-term processor, operating in the DMA mode. Typical information to be recorded for various events includes times and dates of episodes (such as fibrillation episodes or defibrillation pulses in the absence of fibrillation), ten seconds of precursor ECG, capacitor charge times (for example, for each fibrillation pulse), ninety seconds of post-pulse (post-fibrillation pulse) ECG, and various other data, as required by the attending physician, such capability being readily available merely by externally pre-programming the implanted heart stimulator device.

A plastic warning mode of operation constitutes a further short-term mode of operation performed by the more sophisticated of the two processors. In accordance with this mode of operation, a patient warning pulse burst is issued upon detection of ventricular fibrillation. The parameters of this signal are programmable to optimize patient detection, such parameters including burst duration (preferably, rather short), burst amplitude, pulse width, and pulse rate. It is also considered desirable to program the implantable heart stimulator to include a service request pulse burst activated by device fault detection, loss of pacer capture or sensing, low battery voltage, and other similar conditions. The service request signal must be distinguishable from the warning signal, and could, for example, be constituted by two short bursts of a few seconds duration, occurring within ten seconds, and repeated once every hour with amplitude, width and rate programmable, as stated above.

Thus, the implantable heart stimulator and method of the present invention provide the capability of external programming so that various operations, or sequences of operations, can be performed in accordance with various parameters which are capable of being externally set at the discretion of the attending physician.

In general, the implantable heart stimulator according to the present invention comprises an input stage for receiving various status and sensor inputs, a controller section (preferably implemented by a microprocessor) for selectively performing any one of various operations of various types, an output stage responsive to signals provided by the controller for activating the various electrical heart stimulation devices (as well as for activating a patient warning system), and a data input/output channel for receiving and providing, to the controller, data inputs thereto, and for receiving from the controller and providing as an output various data outputs (for example, data to be displayed). In a preferred embodiment, the controller comprises a first controller for selectively performing any one of various operations of a given type, a second controller for selectively performing any one of a plurality of operations of a different type, and an interface for providing exchange of information and control signals between the two controllers.

The implantable heart stimulator and method involve the determination of a condition, from a plurality of conditions, afflicting a patient, the choosing of at least one mode of treatment for treating the condition, and the execution of the steps of each mode or modes of treatment. In a preferred embodiment, the steps or functions just described are repetitively and continuously implemented by the stimulator of the present invention.

Finally, in one embodiment of the implantable heart stimulator and method, a sensing system is provided for sensing the absence of a natural R-wave, as a result of which pacing is performed, and then sensing the presence or absence of a forced R-wave (as would result from successful pacing), the system taking no action in the presence of a forced R-wave, or performing defibrillation in the absence of a forced R-wave.

Therefore, it is an object of the present invention to provide an implantable heart stimulator and method, and more particularly a multi-mode implantable heart stimulator and method capable of accomplishing various types of electrical heart stimulation in response to detection of the occurrence of various heart disorders or arrhythmias.

It is a further object of the present invention to provide a highly versatile implantable heart stimulator capable of performing defibrillation, cardioversion and pacing.

It is a further object of the present invention to provide an implantable heart stimulator which is microprocessor-controlled, and, further, which is externally programmable with respect to various operations, or sequences of operation, to be performed, and various parameters in accordance with which such operations are to be performed.

It is a further object of the present invention to provide an implantable heart stimulator which is not only microprocessor-controlled, but which is controlled by a plurality of processors (for example, in a preferred embodiment, two processors), each processor being specially selected, by virtue of its design, for performing operations of a given type.

It is a further object of the present invention to provide an implantable heart stimulator controlled by dual processors, one processor being specially selected and designed for the performance of long-term operations, simple in type, while consuming relatively low power, the other processor being selected for the performance of short-term, sophisticated operations, even though consuming relatively high power.

It is a further object of the present invention to provide an implantable heart stimulator controlled by at least one processor which is specially designed for normal operation at a given speed, and which can selectively be actuated to a higher processing speed for the performance of specialized operations requiring high speed of performance.

It is a further object of the present invention to provide an implantable heart stimulator having a data recording device capable of being implanted along with the implantable heart stimulator.

It is a further object of the present invention to provide an implantable heart stimulator and method, wherein absence of a natural R-wave is sensed, as a result of which pacing is performed, followed by sensing of the presence or absence of a forced R-wave, with no further action being taken in the presence of a forced R-wave, and defibrillation being performed in the absence of a forced R-wave.

The above and other objects that will hereinafter appear, and the nature of the invention, will more clearly be understood by reference to the following description, the appended claims, and the accompanying drawings.

BRIEF DESCRIPTION OF THE DRAWINGS

FIG. 4 is a block diagram of the interface 16 and controller 18 of FIG. 1.

FIG. 6 is a flow chart of a typical program exemplifying the types of operations performed by the controller 14 of FIG. 1.

DETAILED DESCRIPTION

The present invention will now be more fully described with reference to various figures of the drawings, FIG. 1 of which is a block diagram of the implantable heart stimulator of the present invention.

Figure 1:
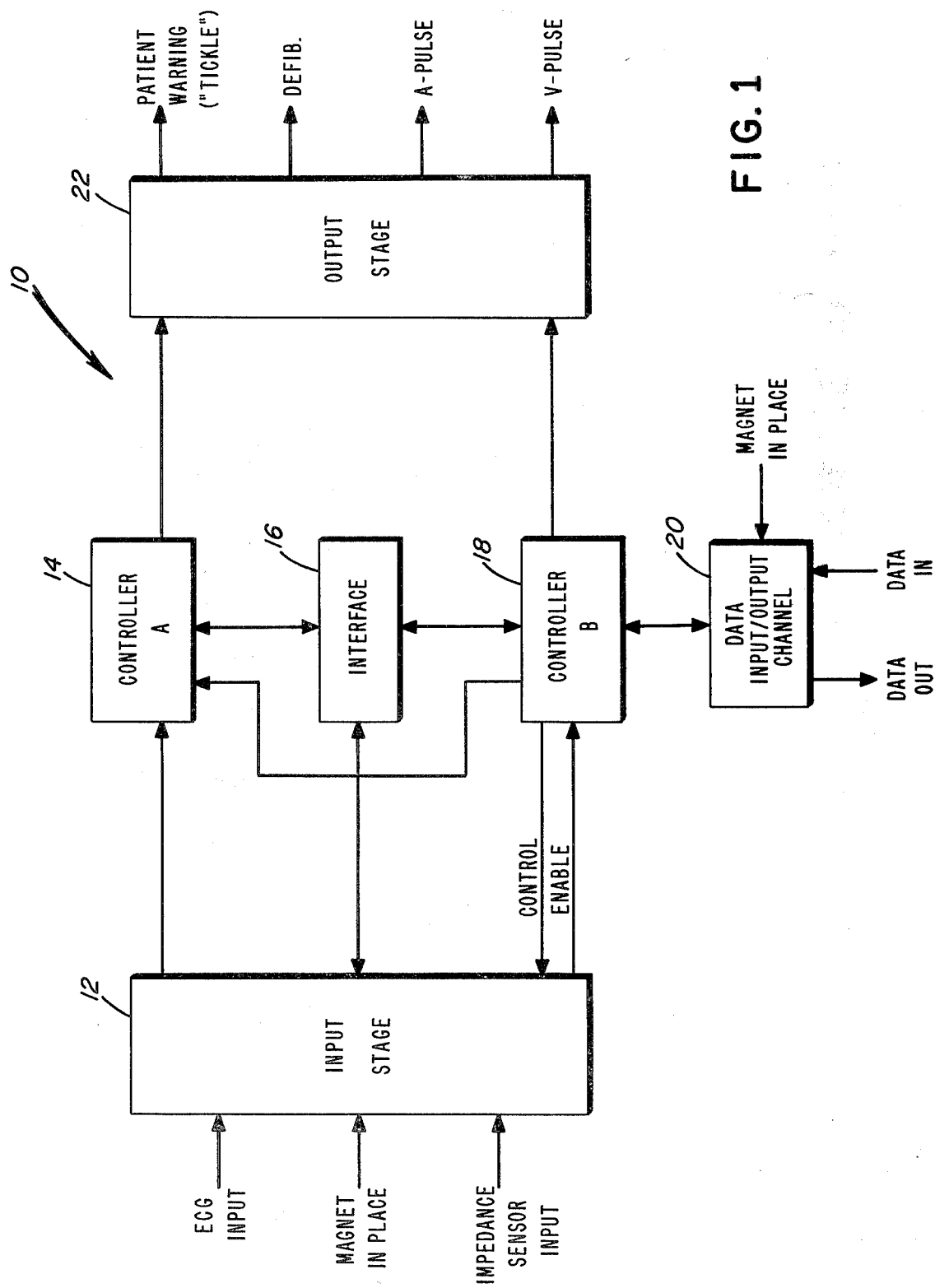
FIG. 1 is a block diagram of the implantable heart stimulator of the present invention.

As seen in FIG. 1, the implantable heart stimulator 10 comprises: an input stage 12 for receiving various sensor and status inputs, that is to say, an impedance sensor input derived from electrodes (not shown) connected to the heart, an electrocardiogram (ECG) input derived from conventional ECG detection and amplifier circuitry (not shown), and an external command signal ("magnet in place") alerting the implantable heart stimulator to the fact that an external command is being received by virtue of placement of a magnet in proximity to the skin, and thus in proximity to (for example) a reed switch (not shown) located just under the skin's surface; a controller (A) 14 which, in response to various signals and inputs received from the input stage 12, as well as from an interface 16 and controller (B) 18 (to be discussed below), performs various operations so as to generate differrent control and data outputs to both an interface 16 and an output stage 22; an interface 16 providing a conduit through which various data, status and control signals pass to and from input stage 12, controller 14 and controller 18; a second controller (B) 18 responsive to various data and control inputs received from input stage 12, interface 16, and a data input/output channel 20, for performing various operations to provide control and data outputs to the input stage 12, the controller 14, the interface 16, the data input/output channel 20, and the output stage 22; a data input/output channel 20 forming a conduit through which both data in and data out pass on their way to or from various elements (visibly, controller 14 and controller 18) of the implantable heart stimulator 10; and an output stage 22 responsive to various control signals from controller 14 and controller 18 for not only actuating conventional defibrillation, cardioverting and pacing devices connected thereto, but also for actuating a patient warning system (to be discussed below).

In accordance with a preferred embodiment of the present invention, controller 14 and controller 18 are specially selected, by virtue of their design, to perform certain, respective operations for which they are particularly suited. This feature of the present invention, including the precise breakdown of functions between controllers 14 and 18, will be discussed in more detail below.

Figure 2A:
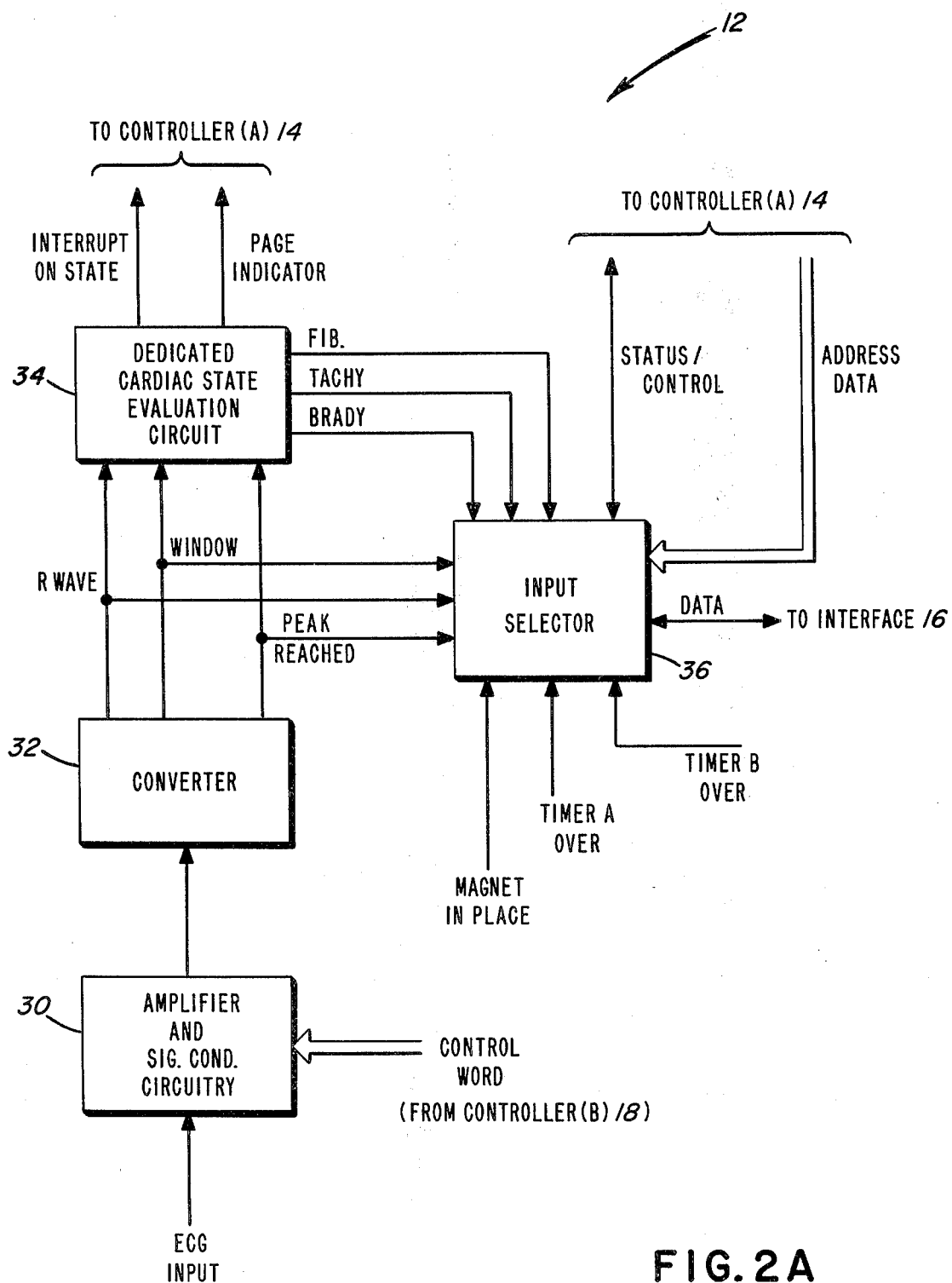
FIGS. 2A, B and C are diagrams relating to the input stage 12 of FIG. 1.
Figure 2B:
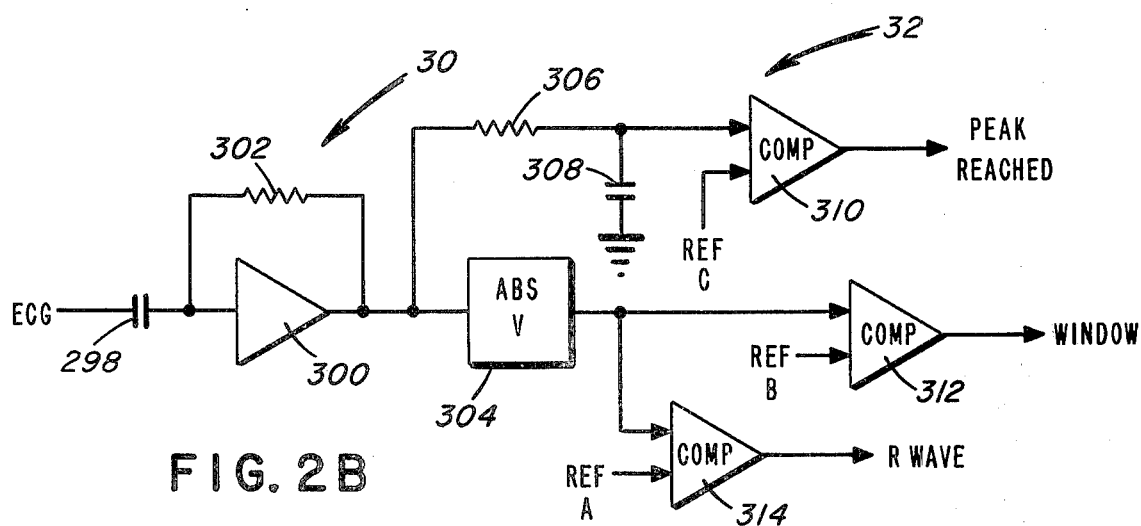
Figure 2C:
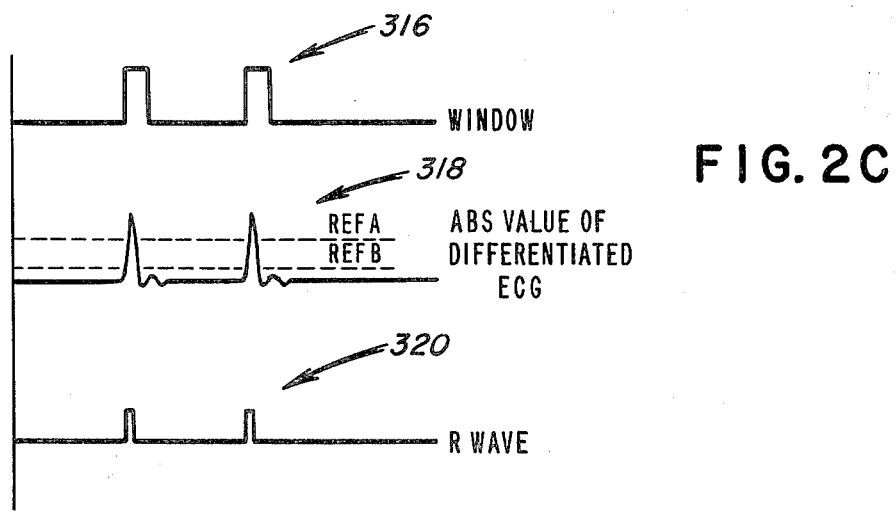

FIGS. 2A, 2B and 2C are diagrams relating to the input stage 12 of FIG. 1. As seen therein, input stage 12 comprises amplifier and signal conditioning circuitry 30, converter 32, a dedicated cardiac state evaluation circuit 34, and an input selector 36.

In operation, amplifier and signal conditioning circuitry 30 receives an ECG input provided by conventional ECG detection circuitry, and performs amplification and signal conditioning (filtering) to provide an analog output. Furthermore, amplifier and signal conditioning circuitry 30 receives an input CONTROL WORD from the controller 18 (FIG. 1), which control input sets the corner frequency for differentiating the ECG input, and also sets the maximum gain which the amplifier can have (thus, setting the sensitivity for the ECG input).

The amplifier and signal conditioning circuitry 30 and the converter 32 of FIG. 2A are shown in more detail in FIG. 2B. As seen therein, the amplifier and signal conditioning circuitry 30 comprises filtering capacitor 298 and a differentiation circuit made up of amplifier 300 and resistor 302. The converter 32 comprises absolute value circuit 304, an RC circuit made up of resistor 306 and capacitor 308, a comparator 310, comparator 312, and comparator 314.

In operation, the input ECG signal is filtered by capacitor 298, and then is differentiated by amplifier 300 and resistor 302. The resulting differentiated ECG signal is provided to an absolute value circuit 304, resulting in generation of the absolute value of the differentiated ECG signal, waveform 318 in FIG. 2C.

The latter waveform is provided to a comparator 314, which receives a reference input REFA, by means of which an output RWAVE (waveform 320 in FIG. 2C) is generated so as to identify the occurrence of each R-wave.

The absolute value of the differentiated ECG signal from absolute value circuit 304 is provided as one input to comparator 312, the other input of which is a reference input REFB, REFB being lower in level than REFA. As a result, comparator 312 generates a further output WINDOW (waveform 316 of FIG. 2C9, thus defining the extent of the waveform 318.

Finally, the differentiated ECG output from comparator 300 is provided, via RC circuit 306, 308, to one input of comparator 310, the other input of which is provided with a reference input REFC. As a result of its operation, comparator 310 generates an output PEAK REACHED, such output identifying each occurrence of a peak in the ECG signal.

Returning to FIG. 2A, dedicated cardiac state evaluation circuit 34 receives digital inputs RWAVE and WINDOW, and produces an interrupt command to the controller (A) 14 (designated INTERRUPT ON STATE). Dedicated cardiac state evaluation circuit 34 also generates, in response to detection of particular cardiac states, corresponding outputs indicating the occurrence of the particular state, that is to say, output FIB (indicating fibrillation), output TACHY (indicating tachycardia), and output BRADY (indicating bradycardia). The latter three outputs are provided to input selector 36.

More specifically, the dedicated cardiac state evaluation circuit 34 comprises circuitry similar to the heart rate circuitry contained in the arrhythmia detection system disclosed in copending application Ser. No. 175,670 filed on Aug. 5, 1980 and fibrillation detection circuitry as in Pat. No. 4,184,493 of Langer et al. Thus, the dedicated cardiac state evaluation circuit comprises circuitry similar to that previously disclosed, such circuitry responding to the RWAVE and WINDOW data inputs thereto for determining which of three states (fibrillation, tachycardia or bradycardia) exists. Moreover, by conventional means (for example, by conventional OR gate circuitry), the dedicated cardiac state evaluation circuit 34 issues an output INTERRUPT ON STATE to the controller 14 whenever any one of the three conditions is detected.

It is also to be noted that conventional logic circuitry can be provided for determining, based on the previously discussed inputs, the existence of various medical conditions, for example, ventricular tachycardia, ventricular fibrillation and super-ventricular tachycardia. Such conventional logic circuitry can be provided either in the dedicated cardiac state evaluation circuit 34, or in one of the processors/controllers to be discussed below. The logic involved will, however, be discussed at this point.

Occurrence of FIB in the absence of TACHY indicates the occurrence of a low-rate tachycardia condition. Conventional medical technique calls for no electrical shock to be administered to a patient afflicted with this condition. However, under these conditions, a "wake-up" call to the controller 18 is issued via the interface 16 and sophisticated pacing modes may begin if so programmed.

Occurrence of both FIB and TACHY indicates a ventricular fibrillation condition, and again a "wake-up" signal is sent to the controller 18 via the interface 16. In addition, controller 14 (FIG. 1) is actuated to cause a defibrillation shock to be issued to the patient via the output stage 22. More specifically, and as will be discussed below, the controller 14 fetches the energy required for defibrillation from a parameter memory (also to be discussed below), transmits such information to a defibrillation pulse generator, shuts down pacing circuits, and issues various other control outputs so as to cause a defibrillation shock to be built up and then applied to the patient (as opposed to a test load). The controller 18, during this time period, is involved in recording parameters surrounding the issuance of the defibrillation shock, such data being provided to the controller 18 via the data input/output channel 20 (FIG. 1).

It is to be noted that, during defibrillation shock of the patient, a sync output is provided to the output stage 22 (specifically, to a pulse generator contained therein) from the interface 16 (specifically, from an output latch contained therein) so that a determination can be made as to whether or not the pulse generator is synchronized (for example, synchronized with RWAVE). Thus, the sync line is kept high at all times during ventricular defibrillation.

Occurrence of output TACH in the absence of output FIB indicates a super-ventricular tachycardia condition, that is, a condition during which the heart beat is rapid but the known probability density function criteria is not fulfilled. In such an instance, synchronized cardioversion (that is, cardioversion synchronized with the RWAVE) may be indicated. Accordingly, under such conditions, a mode word contained in a parameter memory (associated with the controller 18) is provided to an input selector (contained within controller 14), such input selector (as will be discussed in more detail below) basically comprising a one-bit processor unit. The controller 14, as will also be explained in more detail below, issues sync pulses which, when high, indicate synchronization with the R-wave. As a result of such sync pulses provided to the output stage 22 (which contains a pulse generator), a voltage is built up and a pulse is issued once SYNC goes "high".

The latter operations will be discussed in more detail below, in connection with a discussion of the detailed diagrams for the controller 14, interface 16, controller 18, data input/output channel 20 and output stage 22 of FIG. 1.

Input selector 36 is, as previously stated above, a single-bit processor which receives the various control inputs previously mentioned (RWAVE, WINDOW, PEAK REACHED, FIB, TACHY and BRADY), as well as other control inputs (MAGNET IN PLACE, TIMER A OVER, TIMER B OVER) generated outside of the input stage 12. In addition, input selector 36 receives and provides various status and control signals from and to, respectively, the controller (A) 14, and receives data from and provides data to the interface 16. Finally, input selector 36 receives address data from the controller 14.

In response to control inputs from the controller 14, input selector 36 selectively routes the aforementioned control inputs (FIB, TACHY, etc.) from the evaluation circuit 34 to the controller 14. Input selector 36 is, as previously mentioned, an input selector for the one-bit processor, otherwise known as a multiplexer chip (for example, a CMOS chip, model no. 14512). Additional functions of the input selector 36 will be described below, as the implantable heart stimulator and method are described in more detail.

Figure 3B:
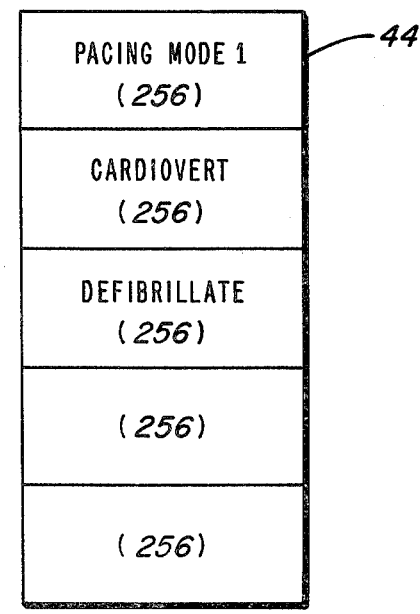
FIGS. 3A and 3B are diagrams relating to the controller 14 of FIG. 1.
Figure 3A:
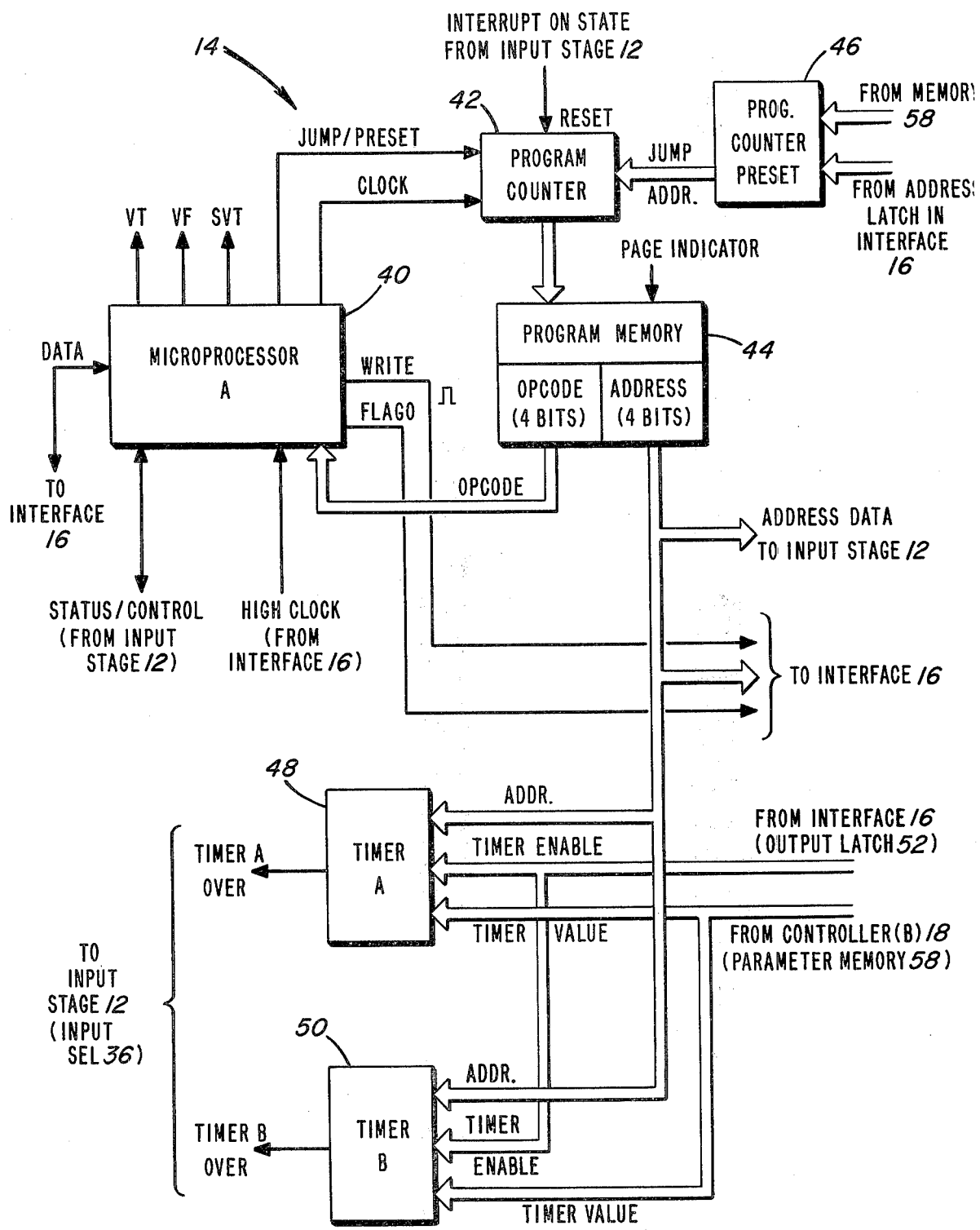

FIGS. 3A and 3B are diagrams relating to the controller (A) 14 of FIG. 1. Controller 14 comprises a microprocessor (A) 40, a program counter 42, program memory 44, program counter preset 46, timer (A) 48, and timer (B) 50.

Microprocessor 40 is, preferably, a control unit of the type generally designated as MC14500B (manufactured by Motorola). However, for the purposes of making and using the present invention, microprocessor 40 may be any similar unit capable of performing relatively simplistic functions on a long-term basis, while consuming relatively low power; e.g., discrete logic can be employed. Microprocessor 40 performs its operations under program control in response to sequentially received operation codes (preferably, of four bits) from the program memory 44.

The microprocessor 40 receives various status and/or control inputs from input stage 12 (specifically, from input selector 36 thereof, as previously discussed), as well as from interface 16 (to be discussed below). Thus, microprocessor 40 need only be capable of reading (and, of course, responding to) such one-bit control inputs. For example, as previously mentioned, microprocessor 40 responds to control input FIB, TACHY and BRADY (provided via input selector 36) to perform the various logic operations discussed above, and to produce corresponding outputs VT, VF and SVT indicating the occurrence of ventricular tachycardia, ventricular fibrillation and super-ventricular tachycardia, respectively.

In addition, in response to such control inputs, and as dictated by the program stored in memory 44, microprocessor 40 performs various other sequential operations (to be discussed in detail below), and in the process generates various control outputs (preferably, one-bit outputs). Notably, microprocessor 40 generates the following control outputs having the indicated functions:

JMP/PRESET—a control output provided to program counter 42 for causing the counter 42 to jump to a given value, thus establishing a given address in memory 44 which is to be accessed for the purpose of providing a given sequence of instructions (op codes) to the microprocessor 40. JMP/PRESET is generated under program control, and causes the "jump address" from preset 46 to be locked into program counter 42. More specifically, the JMP/PRESET command permits execution of a "jump" instruction in accordance with a stored program executed by the controller 14. The program counter preset 46 provides a "jump address" to the program counter 42, the program counter preset 46 consisting of a set of registers (for example, tristate buffers) having low-order bits which define the address bus from program memory 44. It is to be noted that high-order bits which define the address latch (the page to which a jump is to be executed) are provided as input PAGE INDICATOR by evaluation circuit 34 to processor 40. At this juncture, a discussion of the program memory 44 is appropriate.

As seen in FIG. 3B, the program memory 44 may be divided into convenient blocks (for example, of 256 bits size), with each block or page of memory being reversed for a program dealing with a particular one of the conditions which can be experienced by a cardiac patient. Thus, the first block might contain the program for executing a pacing mode, the second block may contain the program for treating a person in need of cardioversion, a third block may contain the program for treating a person in need of defibrillation, and so forth. As mentioned above, the high-order bits of the "jump address" (PAGE INDICATOR) are provided to processor 40 by evaluation circuit 34, and correspond to the particular page or block of memory (set of instructions dealing with a particular condition) to be executed.

Thus, referring back to the discussion of controller 14, with reference to FIGS. 2A and 3A, detection of one of the cardiac conditions by the dedicated cardiac state evaluation circuit 34 results in transmission of control signal INTERRUPT ON STATE to the program counter 42 of controller 14 (FIG. 3A) causing generation of PAGE INDICATOR. The program counter 42 responds to INTERRUPT ON STATE by resetting the low-order bits of the memory address, while PAGE INDICATOR establishes the high-order bits which enable the program counter 42 to page to the beginning of that block in memory 44 corresponding to the desired treatment. Then, the microprocessor 44 responds to successive op codes from the program memory 44 so as to execute the program corresponding to the desired treatment (pacing, cardioversion, defibrillation, and so forth).

CLOCK—a clock-type output provided by microprocessor 40 to the program counter 42, in accordance with which program counter 42 cycles through successive addresses so as to access successive locations in the program memory 44.

WRITE—a pulse output generated by microprocessor 40, and provided to the interface 16. More specifically, whenever the microprocessor 40 in controller 14 determines that data must be provided to certain other elements of the implantable heart stimulator, it issues the WRITE command to the interface 16 (specifically, to an output latch contained therein, and to be discussed below). The interface 16 responds by providing whatever data is contained on the address bus connected to the output latch in interface 16 to the appropriate element (for example, the timers 48 and 50, which receive timer data from the interface 16 (the output latch contained therein)).

An example of such a procedure is as follows: (1) an address (ADDR) is provided from the program memory 44 to the timers 48 and 50 so as to select one of the timers, and to the interface 16 (the output latch contained therein) so as to access data (e.g., TIMER VALUE) in parameter memory 58; (2) the latch responds thereto by accessing the particular address in parameter memory 58, which address contains the data to be transferred; (3) the desired data (for example, timer address data) is made available, via the output latch in interface 16, to the timers 48 and 50; (5) a selected timer, as indicated by the timer address data (ADDR) provided by the program memory 44 to the timers 48 and 50, receives the data (TIMER VALUE) made available by the interface 16; and (6) the particular timer 48 or 50 begins its timing operation. In this manner, such timing information as the atrial escape interval (related to the pacing rate) or ventricular escape interval can be provided, and a timing operation can be conducted in accordance therewith, so as to accomplish various pacing or defibrillation functions. It is to be noted that, as an alternative, an enable signal TIMER ENABLE from controller 18 could be used to select-/enable a given one of the timers 48 and 50.

FLAGO—a control output provided to the interface 16. This control output is used as a strobe to write information into an address latch contained within the interface 16.

STATUS/CONTROL—a general designation for status and control inputs received from and provided to input stage 12; more specifically, various status and control signals selected by input selector 36 (as previously discussed) are provided to the microprocessor 40 of controller 14. These status and control signals relate, for example, to the various medical conditions which might occur: tachycardia, bradycardia, fibrillation, and so forth, as already discussed.

Further referring to FIG. 3, it is to be noted that microprocessor 40 receives a control input HIGH CLOCK from the interface 16. The microprocessor 40 responds to this "high clock" instruction so as to switch its mode of operation into "high gear" in order to perform subsequent processing operations at a higher speed than is normally the case. Conversely, the microprocessor 40, in the absence of the "high clock" instruction, operates in a "low gear" mode of operation so as to perform processing operations at a lower speed, that is, at a normal speed of operation. In this manner, those operations which require high speed of operation can be performed with such high speed of operation, while those operations which may be performed at normal speed may be performed at normal speed of operation, thus saving power by adapting the processing speed to the particular operation being performed.

Finally, microprocessor 40 receives data from and provides data to the interface 16. More specifically, data is transmitted between the microprocessor 40 and the interface 16 by means of a standard data bus, the data line or bus consisting of a line or lines between the microprocessor 40 and a latch in the interface 16. Various positions in the latch are set/reset as determined by the address bus from the program memory 44 to the interface 16. Furthermore, one or more lines are provided between the controller 14 and the input selector 36 (FIG. 2A) so as to pass data from the input selector 36 to the microprocessor 40 (FIG. 3A) during a "read" operation.

As stated previously, program counter 42 is a conventional counter for issuing successive count outputs, derived in accordance with a clock input from the microprocessor 40. Thus, counter 42 accesses successive locations in the program memory 44 for the purpose of providing op code instructions to the microprocessor 40, as well as for the purpose of providing memory addresses to the input stage 12, specifically, to the input selector 36, thus causing input selector 36 to read the desired input line (e.g., FIB, BRADY, etc.) to the interface 16 covered previously, and to the timers 48 and 50 covered previously.

Finally, controller 14 includes a preset circuit 46 which (as previously explained) provides a JUMP ADDRESS output to the program counter 42 to preset the counter 42, thus executing a "jump" instruction.

FIG. 4 is a block diagram of the interface 16 and controller 18 of FIG. 1. As seen therein, the interface 16 comprises an output latch 52 and an address latch 54, both of which were referred to previously. They are conventional latches having multiple positions which can be set by controller 14 and/or input stage 12.

In operation, the output latch 52 effectively receives various control and data inputs from and provides various control and data inputs to the controller 14, receives various data from and provides various data to the input stage 12, and provides various control outputs to the controller 18 and output stage 22, respectively. More specifically, output latch 52 receives or provides the following control signals:

WRITE—a control input (discussed above) which is received from the controller 14, specifically, from microprocessor 40, and which causes the latch 52 to receive/store the data coming from the DATA line, that is, from the microprocessor 40 (FIG. 3A).

HIGH CLOCK—a control output (also discussed above) from output latch 52, which control output causes the microprocessor 40 to perform certain processing operations at a speed higher than normal, with other processing operations being performed at a normal speed, thus conserving power by adapting the speed of processing to the particular operation being carried out.

START DEFIB—a control signal generated by output latch 52 by command of the microprocessor 40, and provided to the output stage 22 (to a pulse generator therein), for the purpose of indicating the need for defibrillation. This control input is generated as a result of logical operations performed in the microprocessor 40; such logical operations were described above with reference to the various control input conditions (FIB, TACHY) which are logically processed so as to determine which medical condition (ventricular tachycardia (VT), ventricular fibrillation (VF), or super-ventricular tachycardia (SVT)) has occurred.

AP1—a control output provided by latch 52 to the output stage 22, indicating the need for atrial pacing activity to take place; it is a control output generated by microprocessor 40.

VEP1—a control output provided by latch 52, and provided to output stage 22, indicating the need for commencement of ventricular pacing activity; it is a control output generated by microprocessor 40.

SELECT PATIENT—a control output generated by latch 52, and transmitted to output stage 22, designating the patient (as opposed to test load), with respect to which defibrillation activity is to be started (per the START DEFIB control signal previously discussed above).

WAKE UP—a control input generated by latch 52, and transmitted to the controller 18 for the purpose of alerting the controller 18 to perform its various control functions (as will be discussed below).

The output latch 52 receives, as previously stated, address data from the controller 14. Output latch 52 also receives data from and provides data to the input state 12, that is, to the input selector 36.

Address latch 54 of interface 16 receives address data and the control input FLAGO from controller 14, and provides parameter address information to the controller 18.

Further referring to FIG. 4, the controller 18 comprises a microprocessor (B) 56 and a pacer-defibrillator parameter memory 58. The microprocessor 56 is, preferably, a microprocessor system 1802 (manufactured by RCA Corporation), but can be any conventional microprocessor capable of performing similar operations. Typically, microprocessor systems capable of sophisticated operations consume relatively high power. The microprocessor 56 should, in accordance with the invention, have the capability of operation in the direct memory access (DMA) mode, such mode of operation being employed in the operation of a precursor memory. More specifically, the processor 56 has a DMA mode, by means of which ECG data is written into a precursor memory, so that the implantable heart stimulator can "look at" the ECG data just prior to fibrillation. This technique is known to those of skill in the art, especially in view of prior application U.S. Ser. No. 902,763 filed on May 3, 1978, now U.S. Pat. No. 4,223,678.

In the latter regard, in operation, the microprocessor 56 periodically executes DMA cycles so as to store ECG data in the precursor memory, such operation being carried out even while the microprocessor 56 is "asleep".

When defibrillation is detected by the microprocessor 40 (FIG. 3A) in controller 14, the precursor memory is "frozen", such that ECG information occurring just prior to defibrillation is available to the microprocessor 56, and thus to the operator of the implantable heart stimulator.

Microprocessor 56 generates, in response to the occurrence of certain conditions, a "patient warning" output, the latter being provided to output stage 22 for the purpose of generating a patient "tickle" signal. Microprocessor 56 also generates outputs AP2 (indicating the need for atrial pacing) and VP2 (indicating the need for ventricular pacing), the latter being provided to output stage 22.

Microprocessor 56 receives a control input, MAGNET IN PLACE, indicating an external command via the placement of a magnet in proximity to a reed switch (not shown) located just under the skin of the patient. This external command to the microprocessor 56 alerts it to the imminent input/output of data, and causes the microprocessor 56 (which is responsible for input/output of data to/from the implantable heart stimulator) to enable the data input/output channel 20 (FIG. 1). In this manner, the processors 40 and 56 can be reprogrammed, or a status word in the parameter memory 58 can be modified. For example, such a status word is provided in the memory 58 for the purpose of indicating which medical procedures (pacing, defibrillation, etc.) are appropriate and permissible for treating a particular patient. Thus, the use of the MAGNET IN PLACE command permits the physician or operator of the implantable heart stimulator to modify the status word in parameter memory 58, and thus modify the particular regimen of treatments which are permissible for the particular patient.

The pacer-defibrillator parameter memory 58 stores parameters necessary for performance of the pacer and defibrillation operations, as is conventionally kown. For example, parameter memory 58 stores information relating to the energy magnitude to be utilized in conjunction with defibrillation, as well as information relating to atrial current and ventricular current to be utilized by the atrial pacer drive circuit 66 and the ventricular drive circuit 68, respectively, in conjunction with pacing operations. As stated previously, the address latch 54 in the interface 16 provides various parameter address informtion to the parameter memory 58, causing selective access of the memory 58 for the purpose of reading out parameter words. The paramter words are, as indicated in FIG. 4, provided to the controller 14 and to the output stage 22. As indicated earlier, these parameter words are provided to the timers 48 and/or 50 in controller 14 for the purpose of setting a destination count in the particular timer so that, when the timer is actuated for counting, a particular interval of time (for example, an AV delay period) will be measured, as a result.

More particularly, the controller 14 (FIG. 3A) includes timers 48 and 50 which are utilized to perform specific timing operations for specific medical treatments. For example, timer 48 could be used for timing the absolute refractory, while timer 50 could be used for timing the pacing (A-V) interval. Timers 48 and 50 each receive address information (ADDR) from the program memory 44, by means of which one or the other timer (or both timers) is (are) selected for carrying out a timing operation. Alternatively, the output latch 52 in interface 16 (FIG. 4) could be utilized to provide a TIMER ENABLE signal to each of the timers 48 and 50, so as to select one or the other (or both) for a timing operation. Finally, the parameter memory 58 in controller 18 provides TIMER VALUE data to each of the timers 48 and 50, such data representing the particular timing values to which the respective timers 48 and 50 are to count.

As indicated, the parameter words are also provided to the output stage 22. For example, parameter words defining energy magnitudes, in accordance with which the defibrillation activities are to be performed, are provided to appropriate circuitry in the output stage 22 (this will be discussed in more detail below, referring to FIG. 5).

It is to be noted that the parameter memory 58 is preferably a dual-port memory or a double-buffered memory. This is desirable in order that the parameters stored in memory remain stable insofar as the processors 40 and 56 are concerned, even while updating procedures are taking place. That is to say, the utilization of a dual-port or double-buffered memory precludes the occurrence of extreme changes in the parameters during ongoing medical procedures, which changes could cause the processors 40 and 56 to function erratically, with possible harm to the patient.

Figure 5:
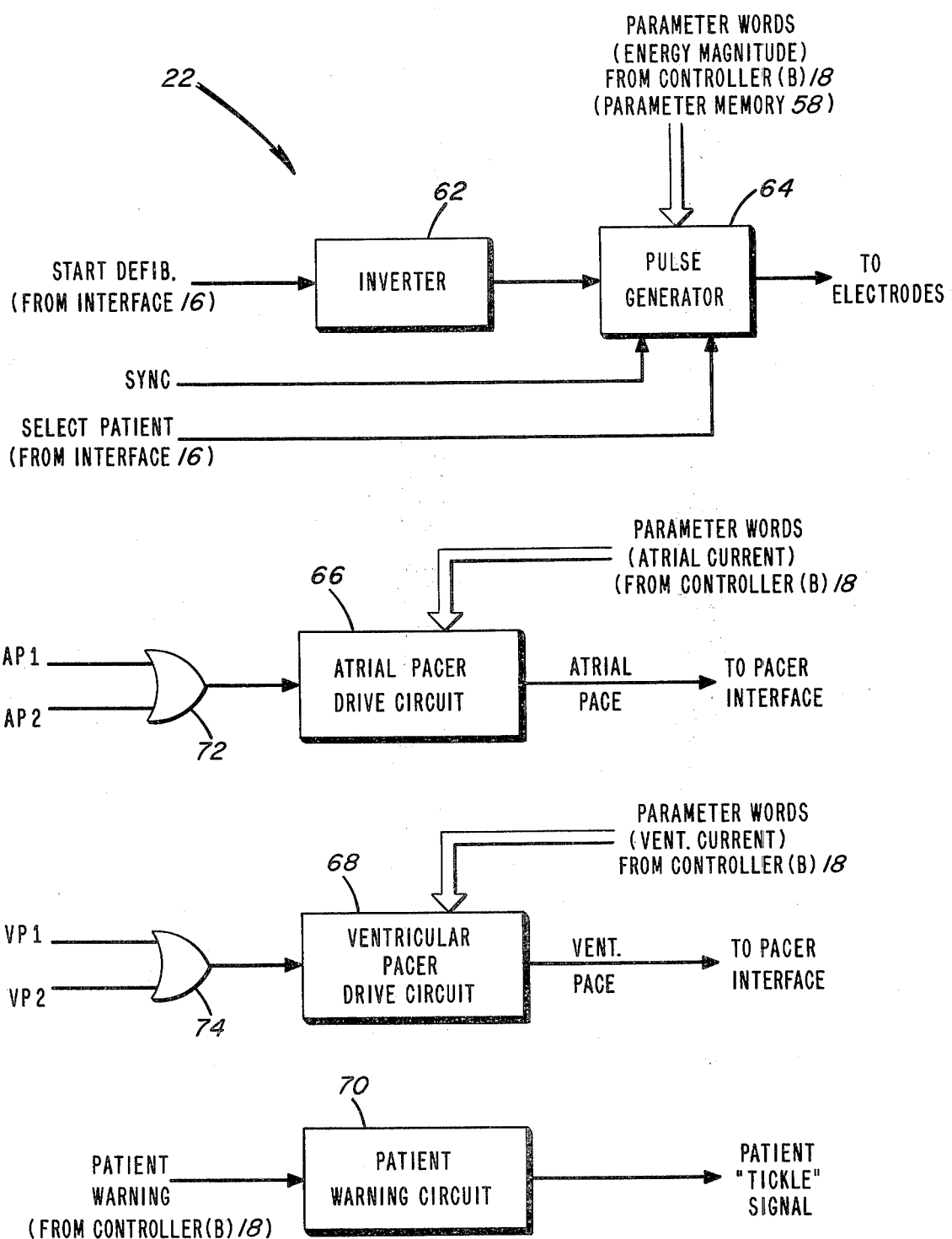
FIG. 5 is a block diagram of the output stage 22 of FIG. 1.

FIG. 5 is a block diagram of the output stage 22 of FIG. 1. As seen in FIG. 5, output stage 22 comprises inverter 62, pulse generator 64, atrial pacer drive circuit 66, ventricular pacer drive circuit 68, and patient warning circuit 70.

In operation, output stage 22 causes the commencement of defibrillation activities in response to the reception, by inverter 62, of the START DEFIB input, provided (as previously discussed) by the output latch 52 of interface 16 (FIG. 4). The START DEFIB input is set by the processor 40 when defibrillation is deemed to be necessary, as previously explained. In response to the START DEFIB input, inverter 62 causes the pulse generator 64 to generate the required defibrillation pulses for transmission to electrodes on or in proximity to the heart (not shown). More specifically, pulse generator 64, in response to inverter 62, generates a defibrillation pulse having an energy magnitude as dictated by the parameter word provided by controller 18, more specifically, by the parameter memory 58 thereof (FIG. 4).

It is to be noted that further detail relative to the inverter 62 and pulse generator 64 in output stage 22 (FIG. 5) is believed to be unnecessary, since the performance of defibrillation techniques utilizing an inverter 62 and a pulse generator 64 are well-known in the art. For example, see prior application Ser. No. 464,180 filed on Apr. 25, 1974, now U.S. Pat. No. 3,952,750, and copending application Ser. No. 65,228 filed on Aug. 9, 1979.

The atrial pacer drive circuit 66 responds to reception of either signal AP1 (from the output latch 52 of interface 16) or the output AP2 (from the microprocessor 56 of controller 18), as received by an OR gate 72, to generate an atrial pace output to a pacer interface (not shown). Similarly, ventricular pacer drive circuit 68 responds to reception of either VP1 (from the output latch 52 of interface 16) or output VP2 (from the microprocessor 56 of controller 18), as received via an OR gate 74, to generate a ventricular pace output to the pacer interface (not shown).

It is to be noted that such a pacer interface is disclosed in copending application Ser. No. 193,027 filed on Sept. 30, 1980, and entitled "Method and Apparatus for Combining Defibrillating and Pacing Functions in a Single Implanted Device", assigned to the assignee of the present invention.

It is also to be noted that, with respect to atrial and ventricular pacing, as carried out by the implantable heart stimulator of the present invention, the output latch 52 of FIG. 4 and the microprocessor 56 of FIG. 4 are each equipped to handle both atrial and ventricular pacing. The specific one of these two elements which performs the atrial or ventricular pacing is dependent on the particular type of pacing to be performed. As mentioned above, the microprocessor 40 (FIG. 3A) operates in conjunction with the output latch 52 to implement atrial and ventricular pacing involving long-term, relatively simple procedures. Conversely, the microprocessor 56 (FIG. 4) handles atrial and ventricular pacing involving short-term, relatively more complicated procedures.

Finally, the patient warning circuitry 70 responds to the reception of a patient warning input (from the controller 18) so as to generate a patient "tickle" signal, alerting the patient that defibrillation is about to take place. Patient warning circuit 70 could, thus, be any conventional circuit for generating a patient "tickle" or similar signal for the purpose of warning the patient of imminent defibrillation.

FIG. 6 is a flowchart of a typical program for implementing the operations of the microprocessor 40 of controller 14 of FIG. 3. In this particular instance, the program relates to simple pacing operations (bifocal pacing) performed under the control of microprocessor 40 of controller 14.

Referring to FIG. 6, block 100, the program is commenced by writing the address of the refractory period to the address latch, such information being provided as input ADDRESS DATA from the controller 14 to the address latch 54 (FIG. 4). In addition, the output FLAG0 is toggled by the microprocessor 40 (FIG. 3), such control output being provided to the interface 16.

Further referring to FIG. 6, block 102, the absolute refractory period from parameter memory 58 (FIG. 4), as accessed by the address latch 54 (under the influence of ADDRESS DATA), is loaded in timer 48 (FIG. 3).

Referring to block 104, a decision is then made as to whether FLAG0 is zero or one. Dependent on which of the two conditions exist, blocks 106 or 108 is implemented so as to write an appropriate address of the pacing interval to the address latch 54. Then, referring to block 110, the appropriate pacing interval is written to the timer 50 (FIG. 3).

Referring to FIG. 6, the logical operation indicated in block 112 is executed, and the program "loops" (blocks 112 and 114) until TIMER A OVER is generated by the time 48 (FIG. 3). As previously stated, this condition is detected by the controller 14 (FIG. 3) via input selector 36 (FIG. 2). Once TIMER A OVER is generated, the microprocessor 40 decides whether or not an R-wave has occurred (block 116). If such has occurred, the "paced beat" flag is cleared (block 118), and a return to block 100 is executed.

The "paced beat" flag can be implemented by merely allocating a particular memory location (one-bit memory location). Alternatively, a one-bit position in output latch 52 can be set aside as the "paced beat" flag, and such flag can be set or cleared by microprocessor 40 (FIG. 3A).

Returning to consideration of FIG. 6 (block 118), if the R-wave has not occurred, the address, in parameter memory 58, of the atrial current is provided to address latch 54, and the atrial current information is loaded from parameter memory 58 to the atrial drive circuit 66 in output stage 22 (FIG. 5), as indicated in block 120 of FIG. 6. Then, referring to block 124, the address, in parameter memory 58, of the pacing pulse width is written to the address latch 54, and the parameter memory 58, as addressed by latch 54, provides the pacing pulse width information to the timer (A) 48 (FIG. 3). However, as indicated in block 124 of FIG. 6, timing of the pacing pulse width by timer 48 is achieved in accordance with 10× (ten times) clocking. That is to say, the programmed operation of microprocessor 40 (FIG. 3)

causes the microprocessor 40 to transmit a control signal to the output latch 52 in interface 16 (FIG. 4). Output latch 52 then generates HIGH CLOCK, the latter being provided to the microprocessor 40 so as to cause it to "gear shift", and microprocessor 40 thus enters the mode of operation whereby processing takes place at a higher than normal speed of operation.

Referring to block 126, the address of the AV (atrial-to-ventricular) pulse delay period is written to address latch 54, and the parameter memory 58, as accessed by address latch 54, writes the AV pulse delay to timer (B) 50 (FIG. 3). Then, referring to blocks 128 and 130, the output latch 52 (FIG. 4) is set, so as to generate output AP1 (provided to the atrial pacer drive circuit 66 via OR gate 72 (FIG. 5)). The output latch 52 remains set so as to generate AP1 until the pacing pulse width set in timer 48 (FIG. 3) is completed. Then, the output latch 52, that is, output AP1, is cleared (block 132), and remains cleared until the AV pulse delay, set in timer 50, is completed (block 134).

Once the AV pulse delay period is completed, a further decision (block 136), as to whether or not the R-wave has occurred, is made. If the R-wave has not occurred, the address, in parameter memory 58, of ventricular current is written to the address latch 54, and parameter memory 58, once accessed by the address latch 54, provides the ventricular current information to the ventricular pacer drive circuit 68 via the OR gate 74 (FIG. 5), as indicated in block 138 of FIG. 6. Then, as indicated by block 140, the address of the pacing pulse width is written to address latch 54 (FIG. 4), and the parameter memory 58 provides the pacing pulse width to the timer (A) 48 (FIG. 3), the latter operating in the "gear shift" or "high clock" mode.

Further referring to FIG. 6, block 142, output latch 52 (FIG. 4) is set so as to generate output VP1, provided to the ventricular pacer drive circuit 68 via OR gate 74 (FIG. 5), and the output latch 52 remains set so as to continuously generate output VP1 until TIMER A OVER occurs at the output of timer 48 (FIG. 3), as indicated by the decision block 144 of FIG. 6. Referring to block 146, once TIMER A OVER is generated, the output latch 52 is cleared, so that output VP1 is no longer applied to the ventricular pacer drive circuit 68 (FIG. 5). Then, referring to block 148, the "paced beat" flag is set to select the proper pacing interval to allow for hysteresis. Hysteresis relates to a change in the pacing rate depending on whether previous beats from the heart were spontaneous or paced. Thus, when previous beats from the heat were paced, the "paced beat" flat (a predesignated memory location or, alternatively, a one-bit position in output latch 52, as discussed above) is set. In this manner, the implantable heat stimulator is able to remain aware of whether or not the previous heat from the heat was spontaneous or paced, thus allowing for hysteresis.

It is to be noted that, referring to block 136 of FIG. 6, if the R-wave has occurred (once TIMER B OVER is generated by the timer 50, as indicated by a "yes" branch from decision block 134), an immediate branch to block 148 is executed, so that the "paced beat" flag is set to select the proper pacing interval to allow for hysteresis. In any event, once block 148 is executed, a branch to the beginning of the pacing routine (block 100) is executed.

As pointed outer earlier, there are certain symptoms, such as the absence of R-waves, that could indicate either ventricular fibrillation or asystole. Because of the desirability of providing protection against both these conditions, a sensing system for ventricular fibrillation can, in one embodiment of the inventive method and system, be provided. For example, such a sensing system can comprise two R-wave detecting circuits. The first R-wave detecting circuit is preferably part of the pacer circuit, and, upon detecting the absence of valid R-waves, sends out pacer spikes in an effort to pace the heart.

Thus, in the case of asystole, the heart would respond by being paced, and would thus develop valid R-waves (forced R-waves) in response to the pacing stimuli. These R-waves are then sensed by a second R-wave detecting circuit (in the sensing system), this second R-wave detecting circuit subsequently controlling a defibrillating sub-system. Thus, in the event of ventricular fibrillation, the operation of the first R-wave detecting circuit in conjunction with the conventional pacing circuit would cause the generation of pacer spikes, but, due to the ventricular fibrillation condition, the heart would be unable to respond to the pacing stimuli. In that eventuality, the second R-wave detecting circuit would note the absence of valid, forced R-waves, and would then diagnose the condition as ventricular fibrillation.

In such an embodiment, an appropriate number of spikes from the second R-wave detecting circuit could be utilized to determine the time of release of the defibrillatory shock. For example, such a shock could be delivered after the twentieth (20th) spike corresponding, for example, to twenty (20) seconds, presuming that each spike is one (1) second apart.

It should be noted that, in such a scheme, the second R-wave detecting circuit must be precluded from responding to the pacing spike of the original pacing unit. This could be accomplished by using an appropriately oriented diode to keep the pacing spikes of the pacing unit (operating in conjunction with the first R-wave detecting circuit) from entering the second portion of the sensing system, that is, the second R-wave detecting circuit. This would, however, cut out half of the signal, and might lead to a problem with certain rhythms having predominantly monophasic complexes.

In the latter regard, it is considered possible to filter out the pacer spike by means of a low-pass filter, thus preventing the spike from getting into the second R-wave detecting circuit. Alternatively, one might choose to protect the amplifier of the second R-wave detecting circuit from the pacer spike by shorting the input thereof during the elaboration of the spike. Indeed, the spike itself could be used to indicate the shorting of the amplifier input, thus ensuring that the second R-wave detecting circuit monitors only during that time when a spike is not present.

In summary, of the three main possibilities or conditions, normal sinus rhythm would cause both the first and second R-wave detecting circuit to remain quiet. Asystole would cause the first R-wave detecting circuit to recognize the absence of R-waves, and the pacer circuit would elaborate spikes causing the paced QRS complexes to occur. If pacing succeeds, the second R-wave detecting circuit would recognize the valid, forced R-waves, and would inhibit further action. However, if pacing does not succeed, the pacer spikes would not cause valid, forced R-waves (indicating ventricular fibrillation), and this condition would be sensed by the second R-wave detecting circuit. As a result, the latter would activate the defibrillation circuit, and would be used to control subsequent defibrillatory shocks, as indicated above.

It is obvious that the embodiments of the present invention described hereinabove are merely illustrative and that other modifications and adaptations thereof may be made without departing from the scope of the appended claims.

What is claimed is:

1. A method of heart stimulation using an implantable heart stimulator capable of detecting a plurality of arrhythmias and capable of being programmed to undergo a single or multi-mode operation to treat a detected arrhythmia, corresponding to said mode of operation the method comprising the steps of:
   (a) determining a condition of the heart from among a plurality of conditions of the heart;
   (b) selecting at least one mode of operation of the implantable heart stimulator which operation includes a unique sequence of events corresponding to said determined condition; and
   (c) executing said at least one mode of operation of said implantable heart stimulator thereby to treat said determined heart condition.

2. The method of claim 1, further comprising the step (d) of repeating said steps (a)–(c), whereby to continuously monitor and treat determined heart conditions.

3. The method of claim 1, wherein said at least one mode of operation of said implantable heart stimulator includes a cardiac pacer mode of operation.

4. The method of claim 1, wherein said at least one mode of operation of said implantable heart stimulator includes cardioversion.

5. The method of claim 1, wherein said at least one mode of operation of said implantable heart stimulator includes automatic defibrillation.

6. The method of claim 1, wherein said at least one mode of operation of said implantable heart stimulator comprises a plurality of unique modes of operation of said implantable heart stimulator corresponding to respective arrhythmias, said method further comprising the step of providing said implantable heart stimulator with dual processors, one of said dual processors being designed to efficiently implement a first group of said plurality of modes of operation of said implantable heart stimulator, and a second one of said dual processors being designed to efficiently implement a second group of said plurality of modes of operation of said implantable heart stimulator.

7. The method of claim 1, wherein said implantable heart stimulator is microprocessor-controlled, said method further comprising the step of externally programming said microprocessor-controlled implantable heart stimulator with respect to said at least one mode of operation thereof.

8. The method of claim 1, wherein said implantable heart stimulator is capable of operation in a cardiac pacer mode of operation and an automatic defibrillation mode of operation;
   said step (a) comprising determining the presence or absence of a naturally induced R-wave of the heart rhythm;
   said step (b) comprising selecting said cardiac pacer mode of operation;
   said step (c) comprising executing said cardiac pacer mode of operation to pace the heart;
   said method comprising the further steps of:
   (d) determining the presence or absence of a forced R-wave;
   (e) selecting, in the absence of said forced R-wave, the automatic defibrillation mode of operation; and
   (f) executing, in the absence of said forced R-wave, said automatic defibrillation mode of operation to automatically defibrillate the heart.

9. The method of claim 8, wherein said step (e) further comprises, in the presence of a forced R-wave, returning to said step (a).

10. An implantable heart stimulator capable of monitoring and detecting a plurality of arrhythmias, and capable of being programmed to undergo a single or multi-mode of operation corresponding to a respective arrhythmia to treat automatically the detected arrhythmia, said stimulator comprising:
    determining means for determining the occurrence of one of a plurality of conditions of the heart;
    selecting means responsive to said determining means for selecting at least one mode of operation of said implantable heart stimulator corresponding to a respective one of said plurality of conditions for automatically treating said determined conditions; and
    executing means for executing a sequence of events defined by said at least one mode of operation, whereby to treat said determined condition.

11. The stimulator of claim 10, wherein said implantable heart stimulator continuously monitors the heart in order to determine the occurrence of any said plurality of conditions.

12. The stimulator of claim 10, wherein said at least one mode of operation includes cardiac pacing.

13. The stimulator of claim 10, wherein said at least one mode of operation includes cardioversion.

14. The stimulator of claim 10, wherein said at least one mode of operation includes aromatic defibrillation.

15. The stimulator of claim 10, wherein said determining means comprises a first detecting circuit for detecting presence or absence of a naturally induced R-wave of the heart, and a second detecting circuit for detecting presence or absence of a forced R-wave of the heart, said selecting means being responsive to absence of said natural R-wave for selecting a cardiac pacer mode of operation, said executing means being responsive to selection of said cardiac pacer mode of operation for pacing the heart, said selecting means being responsive to absence of said forced R-wave for selecting an automatic defibrillation mode of operation, said executing means being responsive to selection of said automatic defibrillation mode of operation for automatically defibrillating the heart.

16. The stimulator of claim 15, wherein said second detecting circuit is actuated to detect the presence or absence of said forced R-wave only after selection and execution of said cardiac pacer mode of operation.

17. The stimulator of claim 16, wherein said selecting means responds to detection of said forced R-wave by inhibiting execution of said automatic defibrillator mode of operation.

18. The stimulator as recited in claim 10 further including a programmable control store for defining a sequence of electrical events corresponding to at least one mode of operation and corresponding operating parameters associated with said mode of operation; and
    an input/output data channel connected to said control store for transferring data therewith which define the sequence of electrical events to be performed by said at least one mode of operation thereby to affect treating operations particularly suited to the patient.

19. The stimulator as recited in claim 18 wherein said programmable control store defines a defibrillating mode of operation and a set of operating parameters including step wise increased energy levels for said defibrillating pulses, said executing means being responsive to said programmable control store to defibrillate the heart in accordance with the programmed mode of operation and the defined operating parameters associated therewith.

20. An implantable heart stimulator for monitoring a heart and treating a plurality of conditions of said heart, comprising:
input means for receiving various status and sensor input signals;
controller means for processing said various status and sensor input signals to determine the occurrence of a given condition from among said plurality of conditions, and for selectively performing a sequence of events defined by at least one mode of operation corresponding to and for treating said determined condition, and issuing corresponding control output signals; and
output means responsive to said control output signals of said controller means for electrically stimulating the heart so as to treat said determined condition.

21. The stimulator of claim 20 wherein said controller selectively performs a plurality of modes of operation and includes first and second processors, said first processor adapted to execute a first group of said plurality of modes of operation so as to treat a first group of a corresponding plurality of conditions, said second processor adapted to execute a second group of said plurality of modes of operation so as to treat a second group of a corresponding plurality of conditions.

22. The stimulator of claim 20, further comprising data input/output channel means for transferring data with said implantable heart stimulator.

23. The stimulator of claim 20 further including an input/output data channel for transferring data with said controller means and wherein said controller means comprises at least one programmable microprocessor for generating said output control signals in dependence on said data signals received through said input/output data channel.

24. The stimulator of claim 20, wherein said output means includes a cardiac pacer.

25. The stimulator of claim 20, wherein said output means includes a cardioverting device.

26. The stimulator of claim 20, wherein said output means comprises an automatic defibrillator.

27. The stimulator of claim 20, wherein said at least one mode of operation includes a cardiac pacer mode of operation and an automatic defibrillator mode of operation, said input means receiving a first sensor input signal corresponding to presence or absence of a naturally induced R-wave of the heart and a second sensor input signal corresponding to presence or absence of a forced R-wave of the heart, said controller means determining the absence of said natural R-wave of the heart and responding thereto by issuing a cardiac pacer control output signal to effect cardiac pacing of the heart, said controller means subsequently determining the presence or absence of said forced R-wave of the heart and responding to the absence thereof by issuing an automatic defibrillation control output signal to effect automatic defibrillation of the heart.

28. The stimulator of claim 27, wherein said controller means responds to the presence of said forced R-wave of the heart by monitoring said R-wave sensor input signal and inhibiting further electrical stimulation of the heart until absence of said naturally induced R-wave of the heart is detected.

29. A stimulator as recited in claim 20 further including
a program control store for defining a sequence of electrical events for at least one operating mode to pace, cardiovert or defibrillate a heart; and
means for further defining at least one parameter associated with said at least one operating mode.

30. A stimulator as recited in claim 29 wherein said defined parameter includes the level of intensity of a pacing signal, defibrillating pulse, or cardioverting pulse.

31. The stimulator as recited in claim 30 wherein the defined sequence of electrical events includes a set of step-wise increased energy levels for said defibrillating, and said executing means issues said defibrillating pulses in successive step-wise increased energy levels until completion of defibrillation.

32. The stimulator as recited in claim 31 wherein the defined parameter includes a preprogrammed number of defibrillating pulses.

33. The stimulator as recited in claim 30 when the defined parameter includes a preprogrammed number of defibrillating pulses.

34. The stimulator as recited in claim 30 wherein the parameters defined by said control store include any combination of the group including the number and level of pulses which treat the heart, perodicity of pulses which treat the heart, tachcardia threshold rate, R-R coupling interval, decrement for R-R coupling interval, width of
said executing means effects treatment of the heart in accordance with at least one of said defined parameters.

35. The stimulator as recited in claim 34 further comprising
an input/output data channel for transferring data with said controller means,
said control means generating said output control signals in accordance with the data signals received through said input/output data channel.

36. The stimulator as recited in claim 29 further comprising
an input/output data channel for transferring data with said control means,
said control means generating said output control signals in accordance with the data signals received through said input/output data channel.

37. The stimulator as recited in claim 20 further including a programmable control store for defining a sequence of electrical events corresponding to at least one mode of operation and associated operating parameters associated with said operation; and
an input/output data channel connected to said control store for transferring data therewith which define the sequence of electrical events to be performed by said at least one mode of operation thereby to affect treating operations particularly suited to the patient.

* * * * *

UNITED STATES PATENT AND TRADEMARK OFFICE

CERTIFICATE EXTENDING PATENT TERM
UNDER 35 U.S.C. § 156

PATENT NO.      : 4,407,288

DATED           : October 4, 1983

INVENTOR(S)     : Alois A. Langer et al.

PATENT OWNER    : Mieczyslaw Mirowski

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

1,107 DAYS from the original expiration date of the patent, December 11, 2000, subject to the requirements of 35 U.S.C. § 41, with all rights pertaining thereto as provided by 35 U.S.C. § 156(b).

I have caused the seal of the Patent and Trademark Office to be affixed this 25th day of April 1996.

Bruce A. Lehman
Assistant Secretary of Commerce and
  Commissioner of Patents and Trademarks

REEXAMINATION CERTIFICATE (4154th)

United States Patent
Langer et al.

[11] B1 4,407,288
[45] Certificate Issued Sep. 19, 2000

[54] IMPLANTABLE HEART STIMULATOR AND STIMULATION METHOD

[75] Inventors: Alois A. Langer, Pittsburgh; Steve A. Kolenik, Leechburg; Marlin S. Heilman, Gibsonia, all of Pa.; Mieczyslaw Mirowski, 2405 Velvet Valley Way, Owings Mills, Md. 21117; Morton M. Mower, Lutherville, Md.

[73] Assignee: Mieczyslaw Mirowski

Reexamination Request:
No. 90/005,165, Nov. 18, 1998

Reexamination Certificate for:
Patent No.: 4,407,288
Issued: Oct. 4, 1983
Appl. No.: 06/243,801
Filed: Mar. 16, 1981

Related U.S. Application Data

[63] Continuation-in-part of application No. 06/215,275, Dec. 11, 1980.

[51] Int. Cl.[7] .................................................. A61N 1/362
[52] U.S. Cl. ..................................................... 607/4; 607/5
[58] Field of Search .............................................. 607/4, 5

[56] References Cited

U.S. PATENT DOCUMENTS

| Re. 27,652 | 5/1973 | Mirowski et al. | 128/419 D |
|---|---|---|---|
| Re. 27,757 | 9/1973 | Mirowski | 128/419 D |

(List continued on next page.)

FOREIGN PATENT DOCUMENTS

| 240961 | 9/1972 | Argentina . |
|---|---|---|
| 0 023 134 A1 | 1/1981 | European Pat. Off. . |
| 2 130 295 | 11/1972 | France . |
| 22 12 591C2 | 10/1972 | Germany . |
| 171 326 | 10/1982 | Netherlands . |
| 389022 | 9/1972 | Sweden . |

| 1 356 190 | 6/1974 | United Kingdom . |
|---|---|---|
| 1 416 197 | 12/1975 | United Kingdom . |
| 1 502 331 | 3/1978 | United Kingdom . |
| 2 002 156 | 2/1979 | United Kingdom . |
| 2 026 870 | 2/1980 | United Kingdom . |

OTHER PUBLICATIONS

"Heart Monitor Automatically Activates Defibrillator," Medical Tribune (Nov. 7, 1968).

B. Peleska, "New Concept for a Universal Implantable Cardiostimulator," Ceskoslovenska Fysilogie (1966) 15(4): pp. 319–323 (1966) (English translation).

(List continued on next page.)

*Primary Examiner*—William E. Kamm

[57] ABSTRACT

An implantable heart stimulator and related method calls for the determination of a given heart condition from among a plurality of conditions, the selection of at least one mode of operation for treating the determined condition, and the execution of the mode of operation selected, so as to treat the determined condition. In one embodiment of the invention, wherein a plurality of modes of operation for treating the various conditions are provided, the implantable heart stimulator includes processors, each processor being designed to efficiently execute a respective group of modes of operation. A further embodiment of the present invention calls for the implantable heart stimulator to be implemented by at least one programmable microprocessor. A still further embodiment calls for the provision of a data input/output channel, by means of which data can be provided to and retrieved from the implantable heart stimulator. Operations carried out by the implantable heart stimulator includes cardiac pacing, cardioversion, and automatic defibrillation. In a further embodiment of the implantable heart stimulator and related method, sensing circuitry is provided to determine the presence or absence of an R-wave of the heart, the absence of which causes a pacing operation to be implemented, further sensing circuitry being provided to determine the presence or absence of a forced R-wave of the heart, the absence of a forced R-wave causing ventricular defibrillation to be implemented.

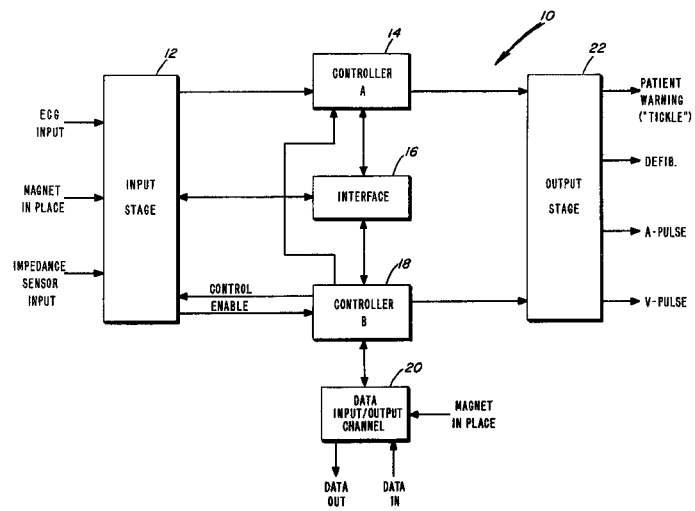

U.S. PATENT DOCUMENTS

| Patent No. | Date | Inventor | Class |
|---|---|---|---|
| Re. 30,372 | 8/1980 | Mirowski et al. | 128/49 D |
| Re. 30,387 | 8/1980 | Denniston, III et al. | 128/419 D |
| Re. 30,750 | 9/1981 | Diack et al. | 128/419 D |
| 3,144,019 | 8/1964 | Haber | 128/2.06 |
| 3,195,540 | 7/1965 | Waller | 128/422 |
| 3,236,239 | 2/1966 | Berkovits | 128/419 |
| 3,241,555 | 3/1966 | Caywood et al. | 128/421 |
| 3,241,556 | 3/1966 | Zacouto | 128/421 |
| 3,253,596 | 5/1966 | Keller, Jr. | 128/421 |
| 3,258,013 | 6/1966 | Druz | 128/419 |
| 3,311,111 | 3/1967 | Bowers | 128/422 |
| 3,389,704 | 6/1968 | Buchowski et al. | 128/419 |
| 3,431,912 | 3/1969 | Keller, Jr. | 128/422 |
| 3,513,850 | 5/1970 | Weber | 128/421 |
| 3,527,228 | 9/1970 | McLaughlin | 128/419 |
| 3,527,229 | 9/1970 | Kempen | 128/419 |
| 3,528,428 | 9/1970 | Berkovits | 128/421 |
| 3,605,754 | 9/1971 | Jaros et al. | 128/419 D |
| 3,614,954 | 10/1971 | Mirowski et al. | 128/419 D |
| 3,614,955 | 10/1971 | Mirowski et al. | 128/419 D |
| 3,631,860 | 1/1972 | Lopin | 128/419 P |
| 3,662,758 | 5/1972 | Glover | 128/419 E |
| 3,693,627 | 9/1972 | Berkovits | 128/419 P |
| 3,698,386 | 10/1972 | Fried | 128/2.06 A |
| 3,703,900 | 11/1972 | Holznagel | 128/419 P |
| 3,716,059 | 2/1973 | Welborn et al. | 128/419 D |
| 3,717,140 | 2/1973 | Greenwood | 128/2.05 T |
| 3,717,153 | 2/1973 | Bowers | 128/419 P |
| 3,718,909 | 2/1973 | Greatbatch | 340/167 A |
| 3,724,455 | 4/1973 | Unger | 128/2.06 A |
| 3,726,285 | 4/1973 | Bowers et al. | 128/419 P |
| 3,727,616 | 4/1973 | Lenzkes | 128/422 |
| 3,738,370 | 6/1973 | Charms | 128/419 D |
| 3,747,605 | 7/1973 | Cook | 128/419 D |
| 3,782,389 | 1/1974 | Bell | 128/419 D |
| 3,798,542 | 3/1974 | Dempsey | 324/133 |
| 3,805,796 | 4/1974 | Terry, Jr. et al. | 128/419 P |
| 3,832,994 | 9/1974 | Bicher et al. | 128/2.06 A |
| 3,833,005 | 9/1974 | Wingrove | 128/419 P |
| 3,857,398 | 12/1974 | Rubin | 128/419 D |
| 3,860,009 | 1/1975 | Bell et al. | 128/419 D |
| 3,862,636 | 1/1975 | Bell elt al. | 128/419 D |
| 3,870,050 | 3/1975 | Greatbatch | 128/419 PG |
| 3,881,467 | 5/1975 | Stanly et al. | 128/2.06 A |
| 3,886,950 | 6/1975 | Ukkestad et al. | 128/419 D |
| 3,888,260 | 6/1975 | Fischell | 128/419 PG |
| 3,920,024 | 11/1975 | Bowers | 128/419 PG |
| 3,924,641 | 12/1975 | Weiss | 128/419 PG |
| 3,939,844 | 2/1976 | Pequignot | 128/419 PG |
| 3,942,534 | 3/1976 | Allen et al. | 128/419 PG |
| 3,942,536 | 3/1976 | Mirowski et al. | 128/419 D |
| 3,945,387 | 3/1976 | Adams | 128/419 PG |
| 4,030,509 | 6/1977 | Heilman et al. | 128/419 D |
| 4,066,086 | 1/1978 | Alferness et al. | 128/421 |
| 4,088,138 | 5/1978 | Diack et al. | 128/419 D |
| 4,097,113 | 6/1978 | McKelvy | 339/256 R |
| 4,126,139 | 11/1978 | Walters et al. | 128/419 PG |
| 4,140,132 | 2/1979 | Dahl | 128/419 PG |
| 4,142,533 | 3/1979 | Brownlee et al. | 128/419 PT |
| 4,146,029 | 3/1979 | Ellinwood, Jr. | 128/260 |
| 4,163,451 | 8/1979 | Lesnick et al. | 128/419 PG |
| 4,164,944 | 8/1979 | Alley, III et al. | 128/419 PG |
| 4,165,749 | 8/1979 | Cansell | 128/419 D |
| 4,169,480 | 10/1979 | Digby et al. | 128/419 PG |
| 4,181,133 | 1/1980 | Kolenik et al. | 128/419 PG |
| 4,184,493 | 1/1980 | Langer et al. | 128/419 D |
| 4,201,219 | 5/1980 | Gonzalez | 128/419 PG |
| 4,202,340 | 5/1980 | Langer et al. | 128/419 D |
| 4,210,149 | 7/1980 | Heilman et al. | 128/419 D |
| 4,222,385 | 9/1980 | Backhouse | 128/419 PG |
| 4,223,678 | 9/1980 | Langer et al. | 128/419 D |
| 4,228,803 | 10/1980 | Rickards | 128/419 PG |
| 4,236,522 | 12/1980 | McDonald et al. | 128/419 PG |
| 4,280,502 | 7/1981 | Baker, Jr. et al. | 128/419 PG |
| 4,291,699 | 9/1981 | Geddes et al. | 178/419 D |
| 4,295,474 | 10/1981 | Fischell | 128/697 |
| 4,300,567 | 11/1981 | Kolenik et al. | 128/419 D |
| 4,312,356 | 1/1982 | Sowton et al. | 128/419 PG |
| 4,375,817 | 3/1983 | Engle et al. | 128/419 D |
| 4,384,585 | 5/1983 | Zipes | 128/419 D |
| 4,388,927 | 6/1983 | Schober | 128/419 PG |
| 4,403,614 | 9/1983 | Engle et al. | 128/419 D |
| 4,421,114 | 12/1983 | Berkovits et al. | 128/419 PG |
| 4,440,172 | 4/1984 | Langer | 128/419 D |
| 4,475,551 | 10/1984 | Langer et al. | 128/419 D |
| 4,485,818 | 12/1984 | Leckrone et al. | 128/419 PG |
| 4,576,170 | 3/1986 | Bradley et al. | 128/419 D |
| 4,958,632 | 9/1990 | Duggan | 128/419 PG |

OTHER PUBLICATIONS

B. Lown et al., "New Method for Terminating Cardiac Arrhythmias: Use of Synchronized Capacitor Discharge," Journal of the American Medical Association, vol. 182, No. 5, (Nov. 3, 1962) pp. 150–157.

M. Mirowski et al., "Miniaturized Implantable Automatic Defibrillator for Prevention of Sudden Death From Ventricular Fibrillation," Proceedings of the Vth International Symposium on Cardiac Pacing, (Mar. 14–18, 1976) pp. 103–106.

M. Mirowski et al., "The Automatic Implantable Defibrillator: Toward the Development of the First Clinical Model," Proceedings of a Symposium on Management of Ventricular Tachycardia–Role of Mexiletine Held in Copenhagen, Denmark, (May 25–27, 1978) pp. 655–664.

M. Mirowski et al., "The Automatic Implantable Defibrillator: A New Avenue," Medical and Surgical Management of Tachyarrhythmias, (ed. W. Bircks et al.) (1980) pp. 71–80.

J. Bourland et al., "An Animal Model For Testing Automatic Defibrillators," Medical Instrumentation, vol. 14, No. 1, (Jan.–Feb. 1980) pp. 15–17.

C. Wiggers, Physiology in Health and Disease, 5th Ed., Lea & Febiger, (1949) pp. 570–572.

W. Mandel et al., "Recurrent Reciprocating Tachycardias in the Wolff–Parkinson–White Syndrome: Control by the Use of a Scanning Pacemaker," Chest, vol. 69, No. 6, (Jun. 6, 1976) pp. 769–774.

M. Mirowski et al., "Standby Automatic Defibrillator: An Approach to Prevention of Sudden Coronary Death," Archives of Internal Medicine, vol. 126, No. 1, (Jul., 1970) pp. 158–161.

M. Mirowski et al., "The Development of the Transvenous Automatic Defibrillator," Archives of Internal Medicine, vol. 129, No. 5, (May 1972) pp. 773–779.

M. Mirowski et al., "Transvenous Automatic Defibrilltor: Preliminary Clinical Tests of Its Defibrillating Subsystem," Transactions of American Society for Artificial Internal Organs, vol. 18, (Apr. 17–18, 1972) pp 520–525.

M. Mirowski et al., "Ventricular Defibrillation through a Single Intravascular Catheter Electrode System," Abstract, Clinical Research, (Apr. 1971) p. 328.

M. Mower et al., "Ventricular Defibrillation with a Single Intravascular Catheter System Having Distal Electrode in Left Pulmonary Artery and Proximal Electrode in Right Ventricle or Right Atrium," Abstract, Clinical Research, (Apr. 1972) p. 389.

M. Mower et al., "Assessment of Various Models of Acetylcholine Induced Atrial Fibrillation for Study of Intra–Atrial Cardioversion," Abstract, Clinical Research, (Apr. 1972) p. 388.

J. Robinson et al., "Ventricular Tachycardia and Fibrillation with Implanted Electrical Pacemakers," British Heart Journal, vol. 27, No. 6, (1965) pp. 937–941.

R. Ruffy et al., "Influence of Acute Coronary Artery Occlusion on Direct Ventricular Defibrillation in Dogs," Medical Instrumentation, vol. 14, No. 1, (Jan.–Feb. 1980) pp. 23–26.

J. Schuder et al., "Ventricular Defibrillation in the Dog with a Bielectrode Intravascular Catheter," Archives of Internal Medicine, vol. 132, No. 1, (Jul. 1973) pp. 286–290.

P. Troup, "Implantable Cardioverters and Defibrillators," Current Problems in Cardiology, vol. 14, No. 12, (Dec. 1989) pp. 675–815.

A. Castellanos et al., "Implantable Pacemakers for Cardiac Tachyarrhythmias", Cardiac Arrhythmias; Mechanisms and Management, (1980) pp. 159–173.

J. Crick et al., "Variation in Tachycardia Termination Window with Posture and Exercise," Abstract, Proceedings of the Second European Symposium on Cardiac Pacing, Florence, Italy, May 4–6, 1981, PACE: Pacing and Clinical Electrophysiology, vol. 4, (May–Jun. 1981) p. A–7.

P. Curry et al., "Dual–Demand Pacing for Refractory Atrioventricular Re–Entry Tachycardia," PACE: Pacing and Clinical Electrophysiology, vol. 2, No. 2, (Mar. 1979) pp. 137–151.

G. Ewy et al., "Electrode System for Permanent Implantable Defibrillators: Transvenous Catheter and Subcutaneous Plate Electrodes," Medical Instrumentation, vol. 12, No. 5, (Sep.–Oct. 1978) pp. 296–300.

S. Furman, "Appraisal and Reappraisal of Cardiac Therapy: Therapeutic Uses of Atrial Pacing," American Heart Journal, vol. 86, No. 6, (Dec. 1973) pp. 835–840.

J. Haft, "Treatment of Arrhythmias by Intracardiac Electrical Stimulation," Progress in Cardiovascular Diseases, (ed. E. Sonnenblick et al.) vol. 16, No. 6, (May–Jun. 1974) pp. 539–568.

D. Krikler et al., "Dual–Demand Pacing for Reciprocating Atrioventricular Tachycardia," British Medical Journal, (May 8, 1976) pp. 1114–1116.

H. Lew et al., "Control of Recurrent Ventricular Fibrillation by Transvenous Pacing in the Absence of Heart Block," American Heart Journal, vol. 73, No. 6, (Jun. 1967) pp. 794–797.

A. Nathan et al., "Clinical Evaluation of an Adaptive Tachycardia Intervention Pacemaker with Automatic Cycle Length Adjustment," PACE: Pacing and Clinical Electrophysiology, vol. 5, No. 2, (Mar.–Apr. 1982) pp. 201–207.

J. Schuder, "The Role of an Engineering Oriented Medical Research Group in Developing Improved Methods and Devices for Achieving Ventricular Defibrillation: The University of Missouri Experience," PACE: Pacing and Clinical Electrophysiology, vol. 16, No. 1, (Jan. 1993) pp. 95–124.

E. Sowton et al., "Use of a Multi–programmable Pacemaker in the Dual Demand Mode: Influence of Pacing Rate on Termination of Tachycardias," European Heart Journal, vol. 1, No. 3, (Jun. 1980) pp. 165–170.

D. Ward et al., "The Response of Regular Re–Entrant Supraventricular Tachycardia to Right Heart Stimulation," PACE: Pacing and Clinical Electrophysiology, vol. 2, No. 6, (Nov. 1979) pp. 586–595.

D. Zipes et al., "Artificial Atrial and Ventricular Pacing in the Treatment of Arrhythmias," Annals of Internal Medicine, vol. 70, No. 5, (May 1969) pp. 885–896.

W. Chardack et al., "Non–Invasive, Magnetically Coupled Control of Pulse Width of Implantable Pacemakers: Its Value in Reduction of Current Drain and Facilitatin of Patient Follow–Up," Cardiac Pacing: Proceedings of the IVth International Symposium on Cardiac Pacing, Groningen, The Netherlands, (Apr. 17–19, 1973) pp. 128–132.

L. Rubin, et al., "The Combined Standby Transvenous Defibrillator and Demand Pacemaker," Abstract, Circulation, vol. 46, No. 4, (Oct. 1972) pp. II–107.

J. Jenkins et al., "Computer Diagnosis of Supraventricular and Ventricular Arrhythmias: A New Esophageal Technique," Circulation, vol. 60, No. 5, (Nov. 1979) pp. 977–985.

L. Rubin et al., "Automatic Defibrillation and Pacing with a Transvenous Electrode," Proceedings of the Fourth New England Bioengineering Conference, (May 7–8, 1976) pp. 427–430.

S. Epstein et al., "Experimental Acute Myocardial Infarction: Characterization and Treatment of the Malignant Premature Ventricular Contraction," Circulation, vol. 47, No. 3, (Mar. 1973) pp. 446–454.

J. Spann, Jr. et al., "Arrhythmias in Acute Myocardial Infarction: A Study Utilizing an Electrocardiographic Monitor for Automatic Detection and Recording of Arrythmias," The New England Journal of Medicine, vol. 271, No. 9, (Aug. 27, 1964) pp. 427–431.

R. Iyengar et al., "Continuous Monitoring of Ambulatory Patients with Coronary Disease," Progress in Cardiovascular Diseases, vol. 13, No. 4, (Jan. 1971) pp. 392–404.

J. Fisher et al., "Appraisal and Reappraisal of Cardiac Therapy: Cardiac Pacing and Pacemakers II, Serial Electrophysiologic–Pharmacologic Testing for Control of Recurrent Tachyarrhythmias," vol. 93, No. 5, (May 1977) pp. 658–668.

J. Jenkins et al., "Extension of a Single–Beat Algorithm Into Classification of Arrhythmias in Context," Computers in Cardiology, (Sep. 29–Oct. 1, 1977) pp. 305–309.

L. Watkins, Jr., et al., "Implantation of the Automatic Defibrillator: The Subxiphoid Approach," The Annals of Thoracic Surgery, vol. 34, No. 5, Seventh Annual Meeting of Society of Thoracic Surgeons, (Jan. 17–19, 1983) pp. 515–520.

M. Heilman et al., "Analysis of Four Implantable Electrode Systems for Automatic Defibrillator," Abstract, Supplement II to Circulation: An Official Journal of the American Heart Association, vol. 51–52 (Oct. 1975) p. II–194.

A. Langer et al., "A Novel Ventricular Fibrillation Detector for Implantable Defibrillator," Abstract, Supplements to Circulation: An Official Journal of the American Heart Association, vol. 51–52, Jan.–Dec. 1975) pp. II–1, II–205.

A. Langer et al., "Considerations in the Development of the Automatic Implantable Defibrillator," Medical Instrumentation, vol. 10, No. 3, (May–Jun. 1976) pp. 163–167.

B. Lown et al., "Implanted Standby Defibrillators," Circulation: An Official Journal of the American Heart Association, vol. 46, (Oct. 1972) pp. 637–639.

B. Lown et al., "Approaches to Sudden Death from Coronary Heart Disease," Circulation: An Official Journal of the American Heart Association, vol. 44, (Jul. 1971) pp. 130–142.

B. McCallister et al., "Paroxysmal Ventricular Tachycardia and Fibrillation Without Complete Heart Block: Report of a Case Treated with a Permanent Internal Cardiac Pacemaker," The American Journal of Cardiology, vol. 18, (Jul.–Dec. 1966) pp. 898–903.

M. Mirowski et al., "The Automatic Implantable Defibrillator: Some Historical Notes," Cardiac Arrhythmias: Where to Go From Here? (ed. W. Brugada et al.), (1987) pp. 655–662.

M. Mirowski et al., "Feasibility and Effectiveness of Low–Energy Catheter Defibrillation in Man," Circulation: An Official Journal of the American Heart Association, vol. 47, (Jan.–Jun. 1973) pp. 79–85.

M. Mirowski et al., "Implanted Defbrillators," Cardiac Defibrillation Conference, (Oct. 1–3, 1975) pp. 93–96.

A. Moss et al., "Termination and Inhibition of Recurrent Tachycardias by Implanted Pervenous Pacemakers," Circulation: An Official Journal of the American Heart Association, vol. 50, (Jul–Dec. 1974) pp. 942–947.

J. Schuder et al., "Ventricular Defibrillation in the Dog Using Implanted and Partially Implanted Electrode Systems," The American Journal of Cardiology, vol. 33, (Feb. 1974) pp. 243–247.

J. Schuder et al., "Ventricular Defibrillation with Catheter Having Distal Electrode in Right Ventricle and Proximal Electrode in Superior Vena Cava," Abstract, Supplement No. 2 of Circulation: An Official Journal of the American Heart Association, vols. 43 and 44, (Oct. 1971) p. II–99.

R. Spurrell et al., "An Implanted Atrial Synchronous Pacemaker with a Short Atrioventricular Delay for the Prevention of Paroxysmal Supraventricular Tachycardias," Journal of Electrocardiology, vol. 9, No. 1, (1976) pp. 89–96.

W. Tacker et al., "Electrical Defibrillation," CRC Press, Chapter 10, (1980) pp. 167–178.

D. Zipes et al., "Early Experience with an Implantable Cardioverter," The New England Journal of Medicine, vol. 311, No. 8, (Aug. 23, 1984) pp. 485–490.

T. Cheng, "Transvenous Ventricular Pacing in the Treatment of Paroxysmal Atrial Tachyarrhythmias Alternating With Sinus Bradycardia and Standstill," The American Journal of Cardiology, vol. 22, (Jul.–Dec. 1968) pp. 874–879.

J. Crick et al., "Variation in Tachycardia Termination Window With Posture and Exercise," Abstract, Second European Symposium on Cardiac Pacing (May 4–6, 1981), p. A7.

J. Griffin et al., "Clinical Use of an Implantable Automatic Tachycardia–Terminating Pacemaker," American Heart Journal, Part 2, (Dec. 1980) pp. 1093–1096.

D. Heiman et al., "Suppression of Ventricular Arrhythmias by Transvenous Intracardiac Pacing," Journal of the American Medical Association, vol. 195, No. 13, (Mar. 28, 1966) pp. 172–175.

J. Hopps et al., "Electrical Treatment of Cardiac Arrest: A Cardia Stimulator–Defibrillator," Surgery, vol. 36, (Oct. 1954) pp. 833–849.

L. Kappenberger et al., "Programmed Stimulation for Long–Term Treatment and Non–Invasive Investigation of Recurrent Tachycardia," The Lancet, (Apr. 25, 1981) pp. 909–914.

M. Mirowski et al., "Termination of Malignant Ventricular Arrhythmias with an Implanted Automatic Defibrillator in Human Beings," The New England Journal of Medicine, vol. 303, No. 6, (Aug. 7, 1980) pp. 322–324.

G. Ryan et al., "Parodoxical Use of a Demand Pacemaker in Treatment of Supraventricular Tachycardia Due to the Wolff–Parkinson–White Syndrome," Circulation: An Official Journal of the American Heart Association, vol. 38, (Jul.–Dec. 1968) pp. 1037–1043.

E. Sowton et al., "Two Years' Clinical Experience with a Self–Searching Tachycardia Pacemaker" Abstract, The American Journal of Cardiology, vol. 47, (Jan.–Jun. 1981) p. 476.

G. Smith, "Iliofemoral Venous Thrombectomy: Indications, Technique, and Results in Forty–Five Cases," Circulation: An Official Journal of the American Heart Association, vol. 37, (Jan.–Jun. 1968) pp. 847–853.

H. Wellens et al., "Electrical Management of Arrhythmias With Emphasis on The Tachycardias," The American Journal of Cardiology, vol. 41, (May 22, 1978) pp. 1025–1034.

F. Zacouto et al., "On an Electronic Device Whereby the Cardiac Syncope Mechanism in Mammals Can Be Determined and a Corresponding Resuscitation Can Be Implemented," Societe De Biologie, vol. 155, No. 6, (Jun. 24, 1961) pp. 1257–1260, English Translation Attached.

"Line–Operated Synchronized Defibrillators," Health Devices, vol. 2, No. 5, (Mar. 1973) pp. 117–129.

R. Spurrel, "Artificial Cardiac Pacemakers," Cardiac Arrhythmias: The Modern Electrophysiological Approach (ed. D. Krikler et al.) (1975) pp. 238–258.

F. Zacouto et al., "Fundamentals of Orthorhythmic Pacing," Cardiac Pacing: Diagnostic and Therapeutic Tools, (ed. B. Luderitz) (1976) pp. 214–218.

H. Funke, "18 Months of Clinical Experience with the Implantable Optimized Sequential Stimulator (OSS)," Proceedings of the VIth World Symposium on Cardiac Pacing, Montreal (Oct. 2–5, 1979).

N. Smyth et al., "Permanent Pervenous Atrial AV Synchronous and AV Sequential Pacing," Cardiac Pacing: Proceedings of the IVth International Symposium on Cardiac Pacing, Groningen, The Netherlands, (Apr. 17–19, 1973) pp. 143–149.

C. Beck et al., "Ventricular Fibrillation of Long Duration Abolished by Electric Shock," Journal of the American Medical Association, vol. 135, No. 15, (Dec. 13, 1947) pp. 957, 985–986.

L. Geddes et al., "The First Human Heart Defibrillation," The American Journal of Cardiology, vol. 52, No. 3, (Aug. 1983) pp. 403–405.

J. Gullett et al., "Optimum Duration of 60–Hz Current for Direct Ventricular Defibrillation in the Dog," Cardiovascular Research Center Bulletin, vol. 6, No. 3, (Jan.–Mar. 1968) pp. 117–123.

N. Gurvich et al., "Restoration of Heart Rhythm During Fibrillation by a Condenser Discharge," American Review of Soviet Medicine, vol. 4, No. 2, (Dec. 1946) pp. 252–256.

B. Lown et al., "Comparison of Alternating Current with Direct Current Electroshock Across the Closed Chest," The American Journal of Cardiology, vol. 10, No. 2, (Aug. 1962) pp. 223–233.

J. Jude et al., "An Experimental and Clinical Study of a Portable External Cardiac Defibrillator," Surgical Forum: Proceedings of the Forum Sessions Forty–Eighth Clinical Congress of the American College of Surgeons, Atlantic City, New Jersey, (Oct. 1962) pp. 185–187.

M. Mirowski et al., "Clinical Treatment of Life–Threatening Ventricular Tachyarrhythmias with the Automatic Implantable Defibrillator," American Heart Journal, vol. 102, No. 2, (Aug. 1981) pp. 265–270.

L. Watkins et al., "Automatic Defibrillation in Man: The Initial Surgical Experience," The Journal of Thoracic and Cardiovascular Surgery, vol. 82, No. 4, (Oct. 1981) pp. 492–500.

J. Hopps et al., "Electrical Treatment of Cardiac Arrest: A Cardiac Stimulator–Defibrillator," Surgery, vol. 36, (Jul.–Dec. 1954) pp. 833–849.

J. Gold et al., "Contour Graph for Relating Per Cent Success in Achieving Ventricular Defibrillation to Duration, Current, and Energy Content of Shock," American Heart Journal, vol. 98, No. 2, (Aug. 1979) pp. 207–212.

J. Jones et al., "Response of Cultured Myocardial Cells to Countershock–Type Electric Field Stimulation," The American Journal of Physiology, vol. 235, No. 2, (Aug. 1978) pp. H214–H222.

G. Jaros et al., "New Approaches to Fibrillation and Defibrillation of the Heart," S.A. Medical Journal, (Jan. 22, 1972) pp. 63–67.

R. Spurrell et al., "Implantable Automatic Scanning Pacemaker for Termination of Supraventricular Tachycardia," The American Journal of Cardiology, vol. 49, (Mar. 1982) pp. 753–759.

D. Ward et al., "Autodecremental Pacing—A Microprocessor Based Modality for the Termination of Paroxysmal Tachycardias," PACE: Pacing and Clinical Electrophysiology, vol. 3, (Mar.–Apr. 1980) pp. 178–191.

J. Fisher et al., "Termination of Ventricular Tachycardia with Bursts of Rapid Ventricular Pacing," The American Journal of Cardiology, vol. 41, (Jan. 1978) pp. 94–102.

C. Vassaux et al., "Cardioversion of Supraventricular Tachycardias," Circulation, vol. 39, (Jun. 1969) pp. 791–802.

A. Waldo et al., "Relevance of Electrograms and Transient Entrainment for Antitachycardia Devices," PACE: Pacing and Clinical Electrophysiology, vol. 7, No. 3, Part II, (May–Jun. 1984) pp. 588–600.

N. Gurvich et al., "Defibrillation of the Heart with Biphasic Electrical Impulses," Cardiology, Russian Journal, No. 7, (1967) pp. 108–112.

G. Ewy et al., "Electrode Catheter for Transvenous Defibrillation," Medical Instrumentation, vol. 10, No. 3, (May–Jun. 1976) pp. 155–158.

J. Schuder et al., "Transthoracic Ventricular Defibrillation with Square–Wave Stimuli: One Half Cycle, One Cycle, and Multicycle Waveforms," Circulation Research, vol. 15, No. 3, (Sep. 1964) pp. 258–264.

W. Tacker et al., "Defibrillation of the Dog Ventricles Using Single and Multiple Half–Sinusoidal Current Pulses," Cardiovascular Research Center Bulletin, vol. 10, No. 2, (Jul.–Sep. 1971) pp. 57–67.

L. Geddes et al., "Ventricular Defibrillation with Single and Twin Pulses of Half–Sinusoidal Current," Journal of Applied Physiology, vol. 34, No. 1 (Jan. 1973) pp. 8–11.

K. Black et al., "Transcutaneous Oxygen as an Indicator of Metabolic Adaptation in Ischemic Skin Flaps," Proceedings of the Association for the Advancement of Medical Instrumentation, 17th Annual Meeting, (May 9–12, 1982) pp. 15–16.

J. Schuder et al., "Asymmetrical Bidirectional Wave Defibrillation in Calves," 35th ACEMB, Philadelphia, PA, (Sep. 22–24, 1982) p. 41.

M. Niebauer et al., "Efficacy and Safety of the Reciprocal Pulse Defibrillator Current Waveform," Journal of the International Federation for Medical & Biological Engineering, vol. 22, No. 1, (Jan. 1984) pp. 28–31.

J. Schuder et al., "Transthoracic Ventricular Defibrillation in the 100 kg Calf with Symmetrical One–Cycle Bidirectional Rectangular Wave Stimuli," IEEE Transactions on Biomedical Engineering, vol. BME–30, No. 7, (Jul. 1983) pp. 415–422.

J. Schuder et al., "Defibrillation of 100 kg Calves with Asymmetrical, Bidirectional, Rectangular Pulses," Cardiovascular Research, vol. 18, No. 7, (Jul. 1984) pp. 419–426.

W. Tacker et al., "Minimum Duration of Capacitor Discharge Current for Indirect Ventricular Defibrillation in the Dog," Cardiovascular Research Center Bulletin, vol. 7, No. 1, (Jul.–Sep. 1968) p. 21–26.

L. Geddes et al., "Engineering and Physiological Considerations of Direct Capacitor–Discharge Ventricular Defibrillation," Journal of International Federation for Medical and Biological Engineering, vol. 9, (1971) pp. 185–198.

J. Schudder et al., "Transthoracic Ventricular Defibrillation with Triangular and Trapezoidal Waveforms," Circulation Research, vol. 19, (Oct. 1966) pp. 689–694.

M. Mirowski, "Low–Energy Catheter Cardioversion of Atrial Tachyarrhythmias," Clinical Research, Abstract, vol. 22, No. 3, (Apr. 1974).

M. Mower et al., "Anatomical Consequences of Low–Energy Intra–Atrial Catheter Shocks," Clinical Research, Abstract, vol. 22, No. 5, (Mar. 1974) p. 291A.

M. Dwyer et al., "Regional Myocardial Blood Flow (MBF) in Transmural Myocardial Infarction," Abstract, Circulation, vol. 44, No. 4, (Oct. 1971) p. II–124.

M. Mower et al., "Ventricular Defibrilation with a Single Intravascular Catheter System Having Distal Electrode in Left Pulmonary Artery and Proximal Electrode in Right Ventricle or Right Atrium," Abstract, Clinical Research, vol. 20, No. 3, (Apr. 1972) p. 389.

M. Mirowski et al., "Transvenous Automatic Defibrillator as an Approach to Prevention of Sudden Death from Ventricular Fibrillation," Heart & Lung: The Journal of Critical Care, vol. 2, No. 6, (Nov.–Dec. 1973) pp. 867–869.

J. Morganroth et al., "The Athlete's Heart: Comparative Left Ventricular Dimensions of Collegiate Athletes Participating in Sports Requiring Isotonic or Isometric Exertion," Clinical Research, Abstract, vol. 22, No. 5, (Dec. 1974) p. 291A.

S. Levine et al., "Ventilatory Response to Tissue Hypoxia IV," Clinical Research, Abstract, vol. 22, No. 3, (Apr. 1974) p. 508A.

M. Mower et al., "Patterns of Ventricular Activity During Catheter Defibrillation," Circulation, vol. 49, (May 1974) pp. 858–861.

M. Mirowski et al., "Low–Energy Catheter Cardioversion of Atrial Tachyarrhythmias," Clinical Research, Abstract, vol. 22, (1974) p. 290A.

M. Mirowski et al., "Prevention of Sudden Coronary Death Through Automatic Detection and Treatment of Ventricular Fibrillation (VF) Using a Single Intravascular Catheter (C) System," Circulation, vols. 42 and 44, (Oct. 1971) p. II–124.

J. Hartlaub, "Electronics in Cardiac Pacemakers," Proceedings of the Association for the Advancement of Medical Instrumentation, 14th Annual Meetings, (May 20–24, 1979) p. 111.

L. Marion, "Programmables Excite Pacer Firms," Electronics, (Mar. 29, 1979) pp. 84–85.

C. Ragsdale, Harry Diamond Laboratories, Army Heart Monitor—Model IV, (Mar. 1970) pp. 1–132.

H. Wellens, Electrical Stimulation of the Heart in the Study and Treatment of Tachycardias, Chapter 7, University Park Press Baltimore, (1971).

E. Sowton, et al., "The Suppression of Arrhythmias by Artificial Pacemaking," The Lancet, Original Articles, London, (Nov. 21, 1964) pp. 1098–1100.

J. Schuder, "Standby Defibrillators," Archives of Internal Medicine, vol. 127, No. 2, (Feb. 1971) p. 317.

J. Schuder et al., "Ventricular Defibrillation in the Dog with a Bielectrode Intravascular Catheter," Archives of Internal Medicine, vol. 132, No. 2, (Aug. 1973) pp. 286–290.

L. Rubin et al., "Automatic Defibrillation and Pacing with a Transvenous Electrode," Biotelemetry, Proceedings of the Fourth New England Bioengineering Conference, (1975) pp. 427–430.

I. Kruse et al., "Clinical Evaluation of a New Atrial Synchronous Ventricular Inhibited Pacemaker," VIth Symposium on Cardiac Pacing, Montreal (Oct. 2–5, 1979).

Intermedics, Inc., "Clinical Investigators Protocol For Intermedics Model 261–01 and Model 262–01, CyberTach™ 60, Multi–Parameter Programmable with Tachycardia Response Pulse Generator and Intermedics Model 525–01 CyberTech Programmer," (Aug. 1979) pp. 1–51.

R. Ripley, "An Overview of the Holter Procedure," Journal of Cardiovascular and Pulmonary Technology, (Aug./Sep. 1978), pp. 30–35.

Letter from M. Heilman to G. Rahmoeller at FDA (Jun. 22, 1976).

Intermedics, Inc., "General Distribution Notice, Subject: CyberTach™ 60," (Sep. 17, 1979).

J. Schuder et al., "Experimental Ventricular Defibrillation With An Automatic and Completely Impalnted System," American Society for Artificial Internal Organs, vol. 16, (1970) pp. 207–212.

W. Holcomb et al., "A Demand Radio Frequency Cardiac Pacemaker," Medical & Biological Engineering, vol. 7, No. 5, (Sep. 1969) pp. 493–499.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–19 is confirmed.

Claim 20 is determined to be patentable as amended.

Claims 21–37, dependent on an amended claim, are determined to be patentable.

New claims 38–48 are added and determined to be patentable.

20. An implantable heart stimulator [for monitoring a heart and treating a plurality of conditions of said heart] *capable of being programmed to undergo a single or multi-mode operation to treat a detected arrhythmia*, comprising:

input means for receiving various status and sensor input signals;

controller means for processing said various status and sensor input signals to determine the occurrence of [a given condition from among said plurality of conditions] *an arrhythmia*, and for selectively performing a sequence of events defined by at least one mode of operation corresponding to and for treating said [determined condition] *arrhythmia*, and issuing corresponding control output signals; and output means responsive to said control output signals of said controller means for electrically stimulating the heart so as to treat said [determined condition] *arrhythmia*.

*38. The method of claim 1, further comprising the step of selecting at least one parameter for each mode of operation.*

*39. The method of claim 1, wherein said multi-mode operation comprises performance of two modes to treat one arrhythmia.*

*40. The method of claim 39, wherein said one arrhythmia is tachycardia.*

*41. The method of claim 40, wherein said two modes comprise pacing and cardioversion.*

*42. The stimulator of claim 10, further comprising parameter selecting means for selecting at least one parameter for each mode of operation.*

*43. The stimulator of claim 10, wherein said mult-mode operation comprises performance of two modes to treat one arrhythmia.*

*44. The stimulator of claim 43, wherein said one arrhythmias is tachycardia.*

*45. The stimulator of claim 44, wherein said two modes comprise pacing and cardioversion.*

*46. The stimulator of claim 20, wherein said multi-mode operation comprises performance of two modes to treat one arrhythmia.*

*47. The stimulator of claim 46, wherein said one arrhythmia is tachycardia.*

*48. The stimulator of claim 47, wherein said two modes comprise pacing and cardioversion.*

\* \* \* \* \*